United States Patent [19]
Levitt et al.

[11] Patent Number: 4,461,640

[45] Date of Patent: Jul. 24, 1984

[54] HERBICIDAL ALKENYL SULFONAMIDES

[75] Inventors: George Levitt, Wilmington, Del.; William T. Zimmerman, Landenberg, Pa.

[73] Assignee: E. I. Du Pont de Nemours and Company, Wilmington, Del.

[21] Appl. No.: 383,323

[22] Filed: Jun. 2, 1982

Related U.S. Application Data

[63] Continuation-in-part of Ser. No. 328,115, Dec. 7, 1981, abandoned.

[51] Int. Cl.³ .................. C07D 239/42; C07D 251/42; A01N 43/66; A01N 43/54

[52] U.S. Cl. .......................................... 71/92; 71/93; 544/211; 544/213; 544/278; 544/312; 544/317; 544/320; 544/321; 544/332

[58] Field of Search ............... 544/320, 321, 331, 332, 544/253, 278; 71/92

[56] References Cited

U.S. PATENT DOCUMENTS 4,342,587  8/1982  Levitt ..................................... 71/92

Primary Examiner—Robert Gerstl

[57] ABSTRACT

Alkenylsulfonylureas have been found to be effective as herbicides and plant growth regulants.

39 Claims, No Drawings

HERBICIDAL ALKENYL SULFONAMIDES

RELATED APPLICATION

This application is a continuation-in-part of copending application U.S. Ser. No. 328,115, filed Dec. 7, 1981 now abandoned.

BACKGROUND OF THE INVENTION

This invention relates to novel alkenylsulfonylureas and their use as pre- or post-emergence herbicides and plant growth regulants.

Netherlands Pat. No. 121,788, published Sept. 15, 1966, teaches the preparation of compounds of Formula (i), and their use as general or selective herbicides,

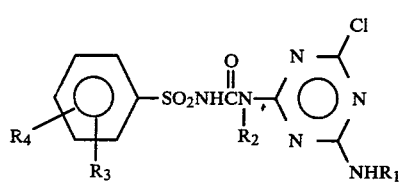

wherein $R_1$ and $R_2$ may independently be alkyl of 1-4 carbon atoms; and $R_3$ and $R_4$ may independently be hydrogen, chlorine or alkyl of 1-4 carbon atoms.

U.S. Pat. No. 3,637,366 discloses compounds having the formula:

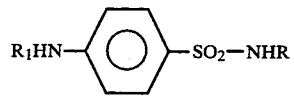

wherein $R_1$ is hydrogen or lower saturated aliphatic acyl; and $R_2$ is hydrogen, 2-pyrimidinyl, pyridyl, amidino, acetyl or carbamoyl.

The disclosed compounds are said to provide control of crabgrass, cress, endive, clover and *Poa annua*.

French Pat. No. 1,468,747 discloses the following para-substituted phenylsulfonamides, useful as antidiabetic agents:

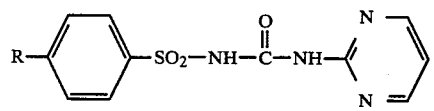

wherein

R=H, halogen, CF_3 or alkyl.

Logemann et al., Chem. Ab., 53, 18052g (1959), disclose a number of sulfonamides, including uracil derivatives and those having the formula:

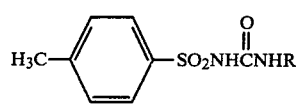

wherein

R is butyl, phenyl or

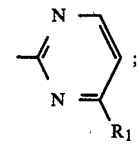

and $R_1$ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121–5 (1962) [Chem. Ab., 59 1633 e] describes the synthesis of N-[(2,6-dimethoxypyrimidin-4-yl)aminocarbonyl]-4-methylbenzenesulfonamide:

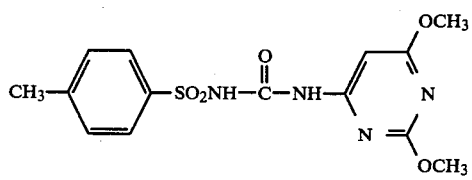

U.S. Pat. No. 4,127,405 teaches compounds which are useful for controlling weeds in wheat having the formula:

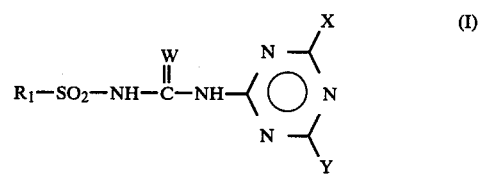

wherein $R_1$ is

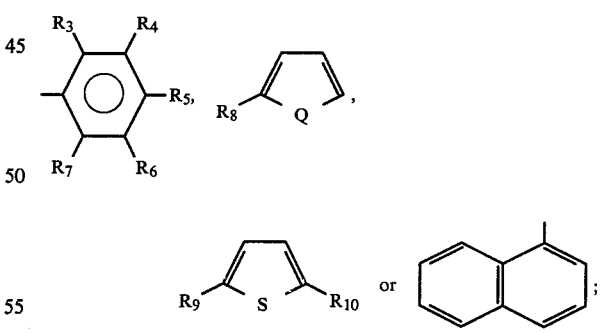

$R_3$ and $R_6$ are independently hydrogen, fluorine, chlorine, bromine, iodine, alkyl of 1-4 carbon atoms, alkoxy of 1-4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1-2 carbon atoms or alkoxy of 1-2 carbon atoms;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S-$ or $CH_3OCH_2-$; and Y is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

The presence of undesired vegetation causes substantial damage to useful crops, especially agricultural products that satisfy man's basic food needs, such as soybeans, barley, wheat, and the like. The current population explosion and concomitant world food shortage demand improvements in the efficiency of producing these crops. Prevention or minimizing the loss of a portion of valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention relates to compounds of Formula I, suitable agricultural salts containing them and their method-of-use as pre-emergent or post-emergent herbicides or plant growth modifiers.

$$LSO_2NHCONA \quad\quad I$$
$$\mid$$
$$R_3$$

where L is 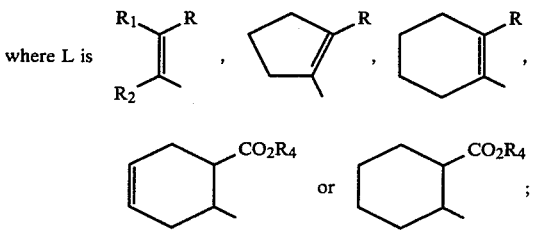

R is F, Cl, Br, $C_1-C_3$ alkyl, $CO_2R_4$, $C(O)SR_8$, $C(O)NR_5R_6$ or $S(O)_mR_7$;

$R_1$ is H, F, Cl, Br or $C_1-C_3$ alkyl;

$R_2$ is H, F, Cl, Br or $C_1-C_3$ alkyl;

$R_3$ is H or $CH_3$;

$R_4$ is $C_1-C_4$ alkyl, $CH_2CH_2OCH_3$, $CH_2CH_2Cl$ or $CH_2CH=CH_2$;

$R_5$ is H or $C_1-C_3$ alkyl;

$R_6$ is $C_1-C_3$ alkyl; or $R_5$ and $R_6$ may be taken together to form $-(CH_2)_4-$, $-(CH_2)_5-$ or $-(CH_2)_2O(CH_2)_2-$;

$R_7$ is $C_1-C_3$ alkyl;

$R_8$ is $C_1-C_4$ alkyl;

m is 0, 1 or 2;

A is

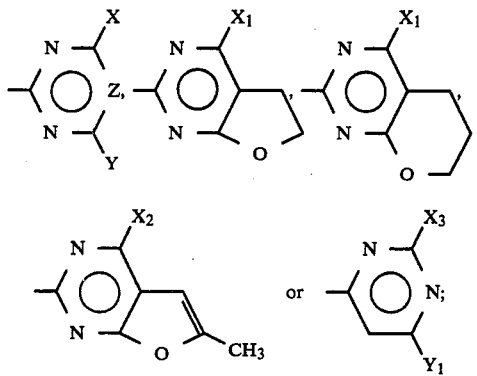

X is Cl, $CH_3$ or $OCH_3$;

Y is $CH_3$, $C_2H_5$, $CH_2OCH_3$, $OCH_3$, $OC_2H_5$, $NH_2$, $NHCH_3$, $N(CH_3)_2$, $CH(OCH_3)_2$ or

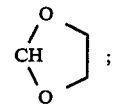 ;

Z is CH or N;

$X_1$ is H, Cl, $CH_3$, $OCH_3$ or $OC_2H_5$;

$X_2$ is $CH_3$, $C_2H_5$, $OCH_3$ or $OC_2H_5$;

$X_3$ is $CH_3$ or $OCH_3$; and $Y_1$ is $CH_3$ or $OCH_3$;

and their agriculturally suitable salts; provided that:

(1) when R is halogen and $R_1$ and/or $R_2$ are halogen, then the values of R, $R_1$ and $R_2$ must be the same;

(2) when $R_1$ and $R_2$ are halogen, then the values of $R_1$ and $R_2$ must be the same;

(3) the total number of carbon atoms of $R_5$ and $R_6$ is less than or equal to 5;

(4) when X is Cl, then Z is CH and Y is $OCH_3$, $NH_2$, $NHCH_3$ or $N(CH_3)_2$;

(5) $R_1$ and $R_2$ are not simultaneously H; and (6) when L is

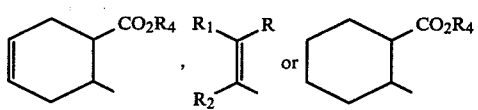

then A is  .

Preferred for their higher herbicidal activity, greater plant growth regulant activity or more favorable ease of synthesis are:

(1) Compounds of Formula I where L is

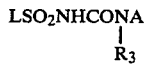

ate alcohol, conveniently used as the solvent, in the presence of an acid catalyst such as sulfuric acid as depicted in Equation 3.

Equation 3

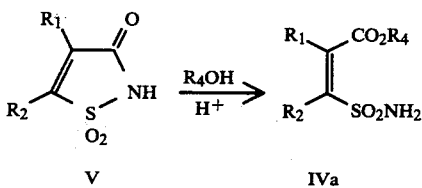

Many of the 3-isothiazolone-1,1-dioxides, V, are described by Lewis et al., J. Het. Chem., 8, 591 (1971).

Many of the sulfonyl chloride precursors to sulfonamides of Formula IV may be prepared by treatment of the corresponding disulfide or benzylthio ether with chlorine in aqueous acetic acid as described by Langler in Can. J. Chem., 54, 498 (1976). The sulfonyl chlorides in which $R_1$ and $R_2$ are taken together to form trimethylene or tetramethylene and R is carbomethoxy are reported by Engberts et al., J. Am. Chem. Soc., 101, 6981 (1979).

In the case of the cyclopentene derivatives where R is carbomethoxy, it is most convenient to react the sulfonyl chloride VI with ammonium hydroxide then with aqueous sodium hydroxide to form the cyclized compound VII. This product is more easily purified by crystallization than the free sulfonamide VIII and it may be readily converted to VIII by the methods described above.

Equation 4

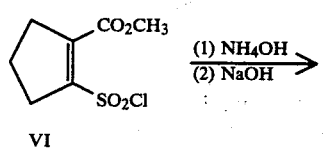

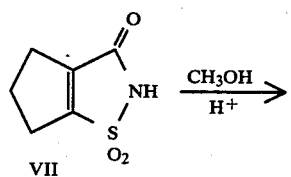

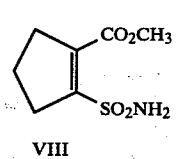

Other sulfonyl chloride precursors to sulfonamides of Formula IV may be prepared by reaction of the appropriate olefin with a sulfonating agent. For example, the treatment of trichloroethylene with chlorosulfonic acid produces trichloroethenesulfonyl chloride IX as disclosed in French Pat. No. 2,094,444.

Equation 5

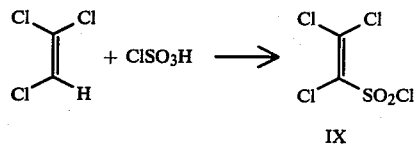

The reaction of isobutylene with phosphorous pentachloride and sulfur trioxide in methylene chloride affords 2-methyl-1-propene-1-sulfonyl chloride as disclosed in Ger. Offen. No. 2,133,793. The synthesis of 2,2-dichloroethenesulfonyl chloride is described in Zh. Obshch. Khim., 41 (11) 25-80 (1971). Also, Ger. Offen. No. 2,133,793 discloses the preparation of 2-chloroethene-1-sulfonyl chloride. Zemlicka and Sorm describe the preparation of 2-chloroethene-1-sulfonamide in Coll. Czech. Chem. Commun., 29, 837 (1964). 1-Bromo-1-propene-1-sulfonyl chloride is prepared as described in Ger. Offen. 2,000,335.

Meyers and Ho [Tetrahedron Letters, 4319 (1972)] describe the preparation of alkenesulfonyl chlorides via a modified Rambert-Bäcklund reaction as shown in Equation 6, where R' and R" are alkyl.

Equation 6

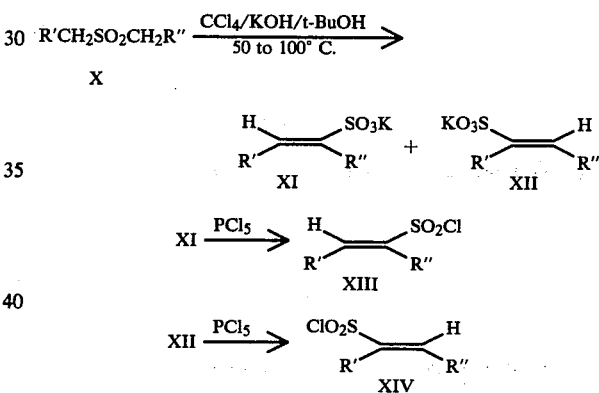

Compounds such as XIII and XIV may be further reacted to form sulfonamides of Formula IV and subsequently to ureas of Formula I. This may be accomplished by isomerization of the double bond present in either IV or I to produce the desired configuration as shown in Equation 7, where $R_1$, $R_2$, $R_3$, R and A are as defined above.

Equation 7

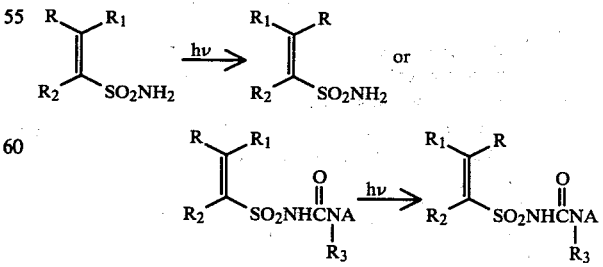

Photoisomerization of alkenes is widely reported in the literature; e.g. A. Schonberg, "Preparative Organic Photochemistry," [Springer-Verlag, New York, (2) Compounds of Formula I where L is

[cyclopentene with R and methyl substituents] or [cyclohexene with R and methyl substituents]

(3) Compounds of preferred 1 where:
R is Cl, Br, $C_1$-$C_3$ alkyl, $CO_2R_4$ or $SO_2R_7$;
$R_4$ is $C_1$-$C_3$ alkyl; and
$R_3$ is H.

(4) Compounds of preferred 3 where
R is $CO_2R_4$.

(5) Compounds of preferred 2 where L is

[cyclopentene with R and methyl substituents]

(6) Compounds of preferred 5 where
R is $CO_2R_4$;
$R_4$ is $C_1$-$C_3$ alkyl; and
$R_3$ is H.

(7) Compounds of preferred 6 where A is

[heterocycle structure with N, X, Z, Y]

(8) Compounds of preferred 2 where L is

[cyclohexene with R and methyl substituents]

(9) Compounds of preferred 8 where
R is $CO_2R_4$;
$R_4$ is $C_1$-$C_3$ alkyl; and
$R_3$ is H.

(10) Compounds of preferred 9 where A is

[heterocycle structure with N, X, Z, Y]

Specifically preferred for their highest herbicidal activity, greatest plant growth regulant activity or most favorable ease of synthesis are:

2-[[(4,6-dimethylpyrimidin-2-yl)aminocarbonyl-]aminosulfonyl]-1-cyclopentene-1-carboxylic acid, methyl ester;

2-[[(4-methoxy-6-methylpyrimidin-2-yl)aminocarbonyl]-aminosulfonyl]-1-cyclopentene-1-carboxylic acid, methyl ester;

2-[[(4,6-dimethoxypyrimidin-2-yl)aminocarbonyl-]aminosulfonyl]-1-cyclopentene-1-carboxylic acid, methyl ester;

2-[[(4,6-dimethyl-1,3,5-triazin-2-yl)aminocarbonyl-]aminosulfonyl]-1-cyclopentene-1-carboxylic acid, methyl ester;

2-[[(4-methoxy-6-methyl-1,3,5-triazin-2-yl)aminocarbonyl]aminosulfonyl]-1-cyclopentene-1-carboxylic acid, methyl ester; and 2-[[(4,6-dimethoxy-1,3,5-triazin-2-yl)aminocarbonyl-]aminosulfonyl]-1-cyclopentene-1-carboxylic acid, methyl ester.

Synthesis

Many of the compounds of Formula I may be synthesized by reacting an appropriately substituted sulfonyl isocyanate of Formula II with an aminoheterocycle of Formula III as depicted in Equation 1, wherein L, $R_3$ and A are as defined above.

Equation 1

$$LSO_2NCO + \underset{\underset{R_3}{|}}{HN}-A \longrightarrow I$$

$$\text{II} \qquad \text{III}$$

The reaction is carried out in a manner analogous to that referred to by Levitt in U.S. Pat. No. 4,169,719 and U.S. Pat. No. 4,127,405.

Preparation of the appropriate sulfonyl isocyanates from the corresponding alkenesulfonamides may be accomplished with n-butyl isocyanate and phosgene in an inert solvent optionally in the presence of 1,4-diazabicyclo[2.2.2]octane (DABCO). The reaction is depicted in Equation 2a and the procedure is again analogous to that referred to by Levitt (loc. cit.) and references therein, as well as in Levitt U.S. Pat. No. 4,238,621.

Equation 2a $$LSO_2NH_2 \xrightarrow[\text{xylenes, DABCO}]{COCl_2, \text{ n-BuNCO}} \text{II}$$

$$\text{IV} \qquad \qquad 140°$$

An alternative process for preparing compounds of Formula I is to react sulfonamides of Formula IV, optionally in the presence of a base, with a heterocyclic carbamate of Formula III'

Equation 2b $$\text{IV} + C_6H_5O\underset{\underset{O}{\|}}{\overset{R_3}{\overset{|}{C}}}N-A \longrightarrow I$$

$$\text{III}'$$

The reaction is carried out in an inert organic solvent such as methylene chloride, dioxane or acetonitrile at elevated temperatures as depicted in Equation 2b, and as disclosed in EPO publication no. 44,807.

The appropriate sulfonamides of Formula IV may be prepared by the action of ammonia or ammonium hydroxide on a sulfonyl chloride as is widely reported in the literature, e.g., Crossley et al., J. Am. Chem. Soc., 60, 2223 (1938). In the cases where R is a carboalkoxy group, the sulfonamides IVa may be prepared by reaction of the cyclic imide of Formula V with the appropri- (1968)], pp. 56–57; and J. G. Calvert, J. N. Pitts, "Photochemistry," [John Wiley & Sons, New York, 1966], pp. 502–504. Often, cis and trans isomeric mixtures result from such processes and the desired cis isomers may be isolated by crystallization, distillation or chromatography at an appropriate stage in the synthetic sequence.

Sulfides of Formula I where R is alkylthio may be prepared from the corresponding chloro or bromo sulfonamides as shown in Equation 8, where $R_1$, $R_2$ and $R_7$ are as previously defined, X' is chloro or bromo, and M is an alkali or alkaline earth metal.

Equation 8

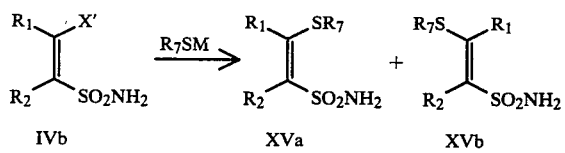

In the case of the acyclic sulfonamides of Formula IVb, an isomeric mixture (XVa and XVb) may result or the undesired isomer XVb may predominate when IVb is reacted with an alkali or alkaline earth metal salt of an alkyl mercaptan. This would again require photoisomerization to produce the desired isomer as discussed in Equation 7.

The preparation of compounds of Formula I where $R=S(O)_mR_7$ and $m=1, 2$ may be accomplished as shown in Equation 9.

Equation 9

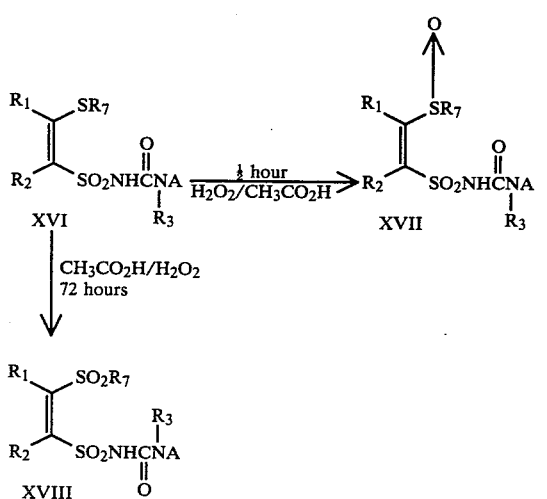

The 2-alkylsulfinyl- and 2-alkylsulfonyl-1-alkene-1-sulfonylureas are made from their corresponding 2-alkylthioalkenesulfonylureas XVI by means of peroxide oxidation. Reaction of the sulfidesulfonylurea XVI with aqueous hydrogen peroxide in acetic acid at room temperature for half an hour affords exclusively the sulfoxidesulfonylurea XVII. If the sulfide or sulfoxide is allowed to react for 72 hours under the same conditions, the sulfone XVIII is obtained. Oxidation for 20 hours often results in a mixture of both sulfoxide and sulfone, which can be readily separated by column chromatography and eluted with ethyl acetate/methylene chloride mixtures. Sulfonylureas described above are generally stable under these reaction conditions. They will however, split into heterocyclic amine and 2-alkylsulfonylalkene-1-sulfonamide if heated. A general procedure for peroxide oxidation of sulfides to sulfones can be found in the paper by A. M. Van Arendonk and E. C. Kliderer, J. Am. Chem. Soc., 62, 3521 (1940).

The compounds of Formula I in which R is alkylthiocarbonyl $[C(O)SR_8]$ or carboxamide $[C(O)NR_5R_6]$ may be prepared from the corresponding methyl ester as shown in Equation 10, wherein the values of $R_1$, $R_2$, $R_3$, $R_5$, $R_6$, $R_8$ and A are as defined above.

Equation 10

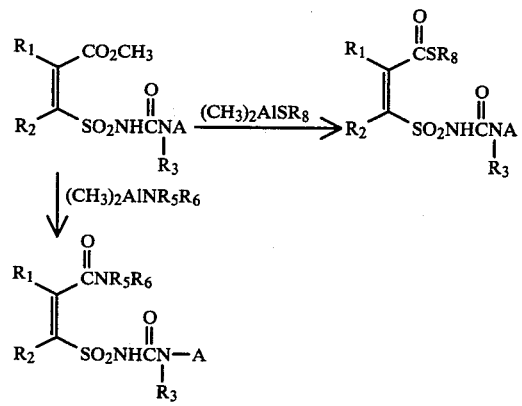

Alkylthiodimethylaluminum or dialkylaminodialkylaluminum is used in these transformations as described in European Patent No. 79-300982.0.

Sulfonamides of Formula IV in which L is 2-alkoxycarbonylcyclohex-4-en-1-yl or 2-alkoxycarbonylcyclohexyl may be prepared as depicted in Equation 11, wherein $R_4$ is as defined previously.

Equation 11

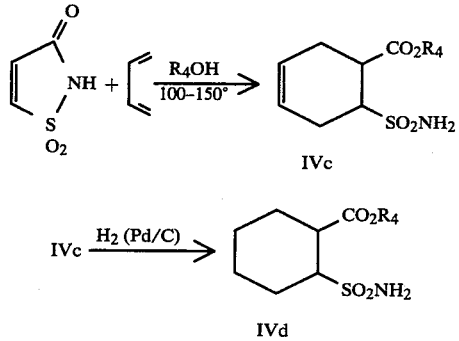

A mixture of excess butadiene and 3-isothiazolone-1,1-dioxide (Lewis et al., loc. cit.) is heated in the appropriate alcohol solvent, $R_4OH$, in an autoclave at 100°–180°, preferably at 130° to 150° for 2 to 12 hours to yield the sulfonamides IVc. These sulfonamides may then be hydrogenated in a suitable inert solvent such as ethyl acetate with a catalyst such as palladium on carbon at ambient temperature to afford the fully saturated sulfonamides IVd.

The synthesis of heterocyclic amines has been reviewed in "The Chemistry of Heterocyclic Compounds" a series published by Interscience Publ., New York and London. 2-Aminopyrimidines are described by D. J. Brown in "The Pyrimidines", Vol. XVI of this series. The 2-amino-1,3,5-triazines are reviewed by K.

R. Huffman and in "The Triazines" of this same series. The synthesis of triazines are also described by F. C. Schaefer, U.S. Pat. No. 3,154,547 and by K. R. Huffman and F. C. Schaefer, J. Org. Chem., 28, 1816–1821 (1963).

Dihydrofuro[2,3-d]pyrimidine-2-amines and dihydropyrano[2,3-d]pyrimidine-2-amines and cyclopentanopyrimidine-2-amines are synthesized as described in European Patent No. 80-300505.7. The substituted 4-aminopyrimidines are disclosed in U.S. Pat. No. 4,221,585.

The preparation of 4,6-dimethylfuro[2,3-d]pyrimidine-2-amine is described by E. Bisagni et al., [Bul. Soc. Chim. Fr., 803 (1969)]. An alternative procedure is depicted in Equation 12 for the case in which $R_3$ is hydrogen and $X_2$ is methyl or ethyl.

Equation 12

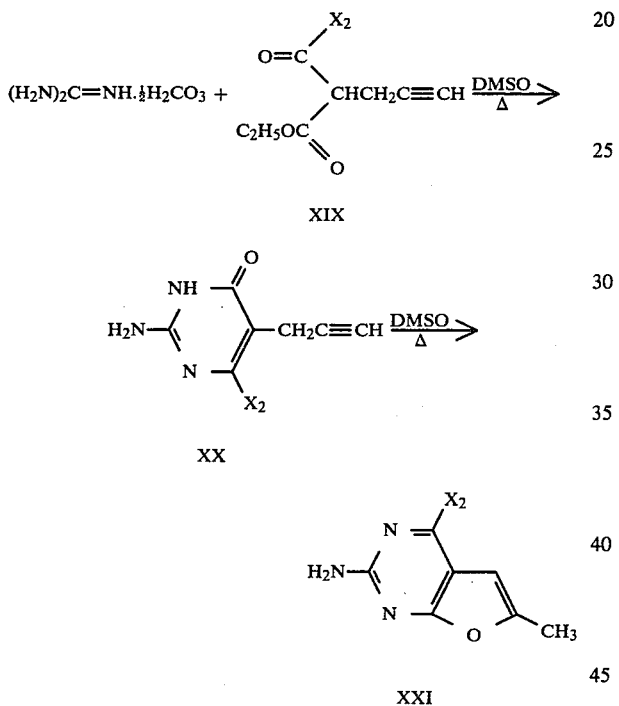

The keto-ester precursors XIX are prepared by well known literature methods, e.g., J. F. Tinker and T. E. Whatmough, J. Amer. Chem. Soc., 74, 5235 (1952).

Reacting XIX with an excess of guanidine carbonate in an organic solvent, preferably a polar aprotic solvent such as dimethylsulfoxide (DMSO), dimethylformamide (DMF), or N,N-dimethylacetamide, at a temperature of 80° to 200°, preferably 100° to 160°, ambient pressure and preferably under an inert atmosphere, yields both XXI and XX as products. The products are isolated upon dilution of the reaction mixture with, for example, acetone and water successively. Higher reaction temperatures and longer reaction times (e.g., in DMSO at 130°–150° for 2 to 8 hours) favor the production of the furopyrimidine XXI over the uncyclized pyrimidine XX.

The intermediates of Formula III in which $X_2$ is methoxy or ethoxy on 2-amino-6-methylfuro[2,3-d]pyrimidine may be prepared from the appropriate malonic ester derivatives XXII, which are known in the art, as shown in Equation 13.

Equation 13

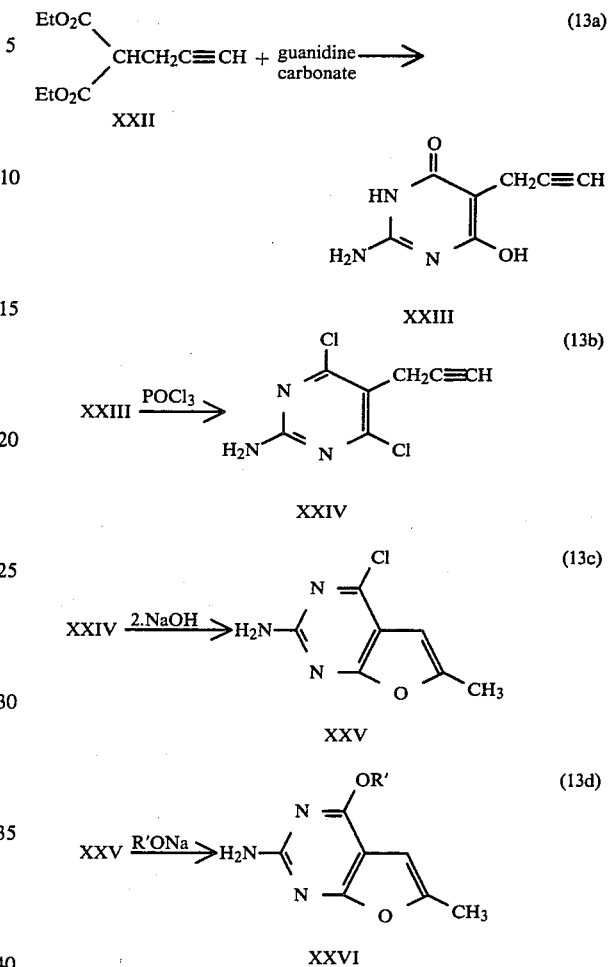

In Equation 13a the diester XXII is reacted with an excess of guanidine carbonate and heated in a suitable solvent such as ethanol or methanol at 50° to 150°, most conveniently at the boiling point of the solvent chosen. The product pyrimidine XXIII is then isolated and contacted with a large excess of phosphorous oxychloride at 50° to 150°, most conveniently at the boiling point of the reaction mixture. The dichloro compound XXIV may be isolated by removal of the excess phosphorous oxychloride under reduced pressure, trituration of the solid residue in ice-water and filtration of the product. Cyclization of XXIV occurs readily in a solvent medium comprised of water and a water-miscible organic solvent such as t-butanol and two equivalents of a base such as an alkali metal hydroxide with heat applied in the range of 50° to 125°. The product is conveniently isolated upon removal of the organic solvent under reduced pressure and filtration of the water-insoluble pyrimidine XXV.

The chloro compound XXV may then be converted to the alkoxy derivative XXVI by heating with an alkali metal alkoxide, e.g., sodium methoxide in methanol solution at temperatures of 20° to 100° C.

Heterocyclic amines of Formula IIIa in which Y is dimethoxymethyl, Z is CH and X is as defined previously are prepared as reported by W. Braker, et al., J.

Am. Chem. Soc., 69, 3072 (1947), and by J. I. De Graw and V. H. Brown, J. Het. Chem., 13, 439 (1976).

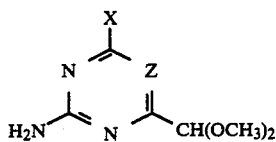

IIIa

Triazines of Formula IIIb may be prepared according to the methods outlined in Equations 14 and 15.

Equation 14

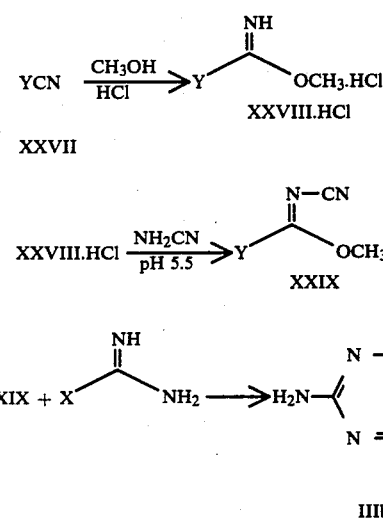

wherein
Y=CH(OCH$_3$)$_2$; and
X=CH$_3$ or OCH$_3$.

Equation 15

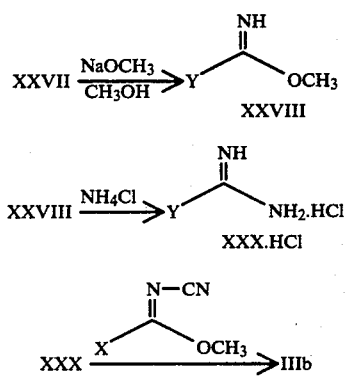

wherein
Y=CH(OCH$_3$)$_2$; and
X=CH$_3$ or OCH$_3$.

The reaction of Equation 14a is carried out according to the teachings of J. M. McElvain and R. L. Clarke, J. Amer. Chem. Soc., 69, 2657 (1947), in which the preparation of ethyl diethoxyiminoacetate is described. The intermediate N-cyanoimidates of Formula XXIX may be prepared according to the teaching of D. Lwowski in Synthesis, 1971, 263, by reacting XXVIII with cyanamide at pH 5.5, and these may be condensed according to reaction 14c with either acetamidine or O-methyl isourea in an alcoholic solvent at 25° to 80° C. to provide the appropriate triazines. Alternatively, the reaction of Equation 15a, described for substituted acetonitriles by F. C. Schaefer and G. A. Peters in J. Org. Chem., 26, 412 (1961), may be used to convert nitriles of Formula XXVII to the corresponding iminoesters. The free base may be carried on through reactions 14b and 14c, or, alternatively, converted to the amidinium hydrochloride salts XXX as described in the aforementioned reference, and condensed with either methyl N-cyanoacetimidate or with dimethyl N-cyano imidocarbonate in the presence of one equivalent of sodium methoxide to provide the triazines of Formula IIIb.

Cyclic acetals of Formula IIIc may be prepared from compounds of Formula IIIa according to Equation 16 by acetal exchange.

Equation 16

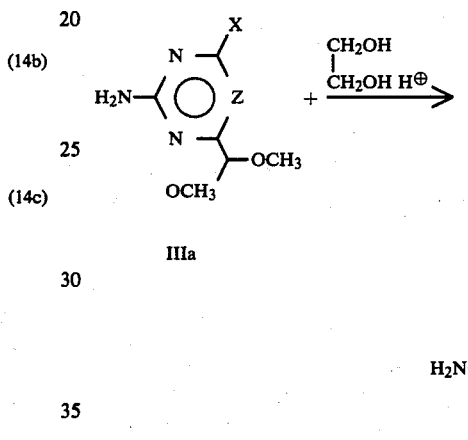

wherein
X is CH$_3$ or OCH$_3$; and
Z is as previously defined.

The reaction of Equation 16 is carried out by heating the acyclic acetal in an inert solvent in the presence of one equivalent of ethylene glycol and slightly more than one equivalent of a strong acid, such as p-toluenesulfonic acid with removal of the methanol formed in the reaction by distillation. The product is isolated by treatment with aqueous base, and extraction with an organic solvent, and purified by crystallization or column chromatography.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation to another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The compounds of this invention and their preparation are further illustrated by the following examples wherein temperatures are given in degrees centigrade.

EXAMPLE 1

5,6-Dihydro-2H-cyclopenta[d]isothiazol-3(4H)-one, 1,1-Dioxide (VII)

A solution of 18 g of methyl 2-(chlorosulfonyl)-1-cyclopentene-1-carboxylate in 400 ml of tetrahydrofuran was cooled to −10°, contacted with 16.2 ml of concentrated ammonium hydroxide, then stirred at 0° for 2.5 hours. The mixture was subsequently acidified with hydrochloric acid, extracted with methylene chloride, then the organic phase was extracted with three 100 ml portions of 1N NaOH. The combined aqueous extracts were decolorized with activated carbon and acidified with 6N HCl, then extracted four times with chloroform. Evaporation of the dried ($Na_2SO_4$) chloroform extract left a residue which was crystallized from benzene/chloroform to yield 4.2 g of the title compound as colorless crystals; m.p. 177°–179°. An infrared spectrum (nujol) exhibited absorptions at 3050, 1730, 1700, 1635, 1330, and 1180 cm$^{-1}$; and the NMR (90 MHz) spectrum in CDCl$_3$/DMSO-d$_6$ solution exhibited absorptions at 2.4–2.9 (m) and 11.3 (br, NH) ppm indicating the title compound.

EXAMPLE 2

Methyl 2-(Aminosulfonyl)-1-cyclopentene-1-carboxylate (VIII)

A solution of 4.2 g of 5,6-dihydro-2H-cyclopenta[d]isothiazol-3(4H)-one, 1,1-dioxide in 75 ml methanol plus 0.5 ml concentrated sulfuric acid was heated to reflux for 1 hour then stirred at ambient temperature for 12 hours. Sodium bicarbonate (2.1 g) was then added, the mixture was filtered and the filtrate evaporated in vacuo to a gelatinous mass. This residue was extracted in chloroform and washed with water and subsequently dried ($Na_2SO_4$), evaporated, and crystallized from ether/hexane to afford 4.4 g of VIII as a white solid; m.p. 83°–84°. An infrared spectrum (nujol) exhibited absorptions at 3300, 3200, 1705, 1630, 1330, 1160 cm$^{-1}$ and an NMR (60 MHz) spectrum in CDCl$_3$ solution exhibited absorptions at 2.05 (CH$_2$), 2.95 (CH$_2$×2), 3.85 (CH$_3$O), and 5.78 (NH$_2$, br) ppm indicating the title compound.

EXAMPLE 3

2-Carbomethoxy-1-cyclopentene-1-sulfonyl Isocyanate

In 75 ml of dry xylenes was placed 4.0 g of methy 2-(aminosulfonyl)-1-cyclopentene-1-carboxylate (VIII), 6.5 ml of n-butyl isocyanate, and 0.05 g of DABCO. The mixture was heated to reflux (ca 138°) then contacted with an excess of phosgene which was condensed into the mixture from a dry-ice condenser until the reflux temperature dropped to 126°. Over several hours the temperature increased to 135° and additional phosgene was condensed into the mixture, again, lowering the temperature to 129°. This process was repeated until no temperature increase could be observed, indicating complete consumption of the sulfonamide. The mixture was then cooled and the xylenes removed under reduced pressure to yield ca 5 g of an amber oil. An infrared spectrum (neat) exhibited a strong absorption at 2230 cm$^{-1}$ indicating the title compound.

EXAMPLE 4

Methyl 2-[[(4-Methoxy-6-methylpyrimidin-2-yl)aminocarbonyl]aminosulfonyl]-1-cyclopenten-1-carboxylate The sulfonyl isocyanate product (5 g) of Example 3 was diluted to a concentration of 1.5M with dry acetonitrile and 2.0 ml of this solution was added to a stirred suspension of 0.31 g 4-methoxy-6-methylpyrimidine-2-amine in 4.0 ml of dry acetonitrile under a nitrogen atmosphere at room temperature. After stirring several hours, the mixture was diluted with ether to precipitate the product which was collected by filtration and dried; m.p. 161°–163°. An infrared spectrum (nujol) exhibited absorptions at 1730 and 1700 cm$^{-1}$, and an NMR (90 MHz) in CDCl$_3$ solution exhibited absorptions at 2.1 (CH$_2$), 2.45 (CH$_3$), 3.0 (CH$_2$×2), 3.75 (CH$_3$O), 3.95 (CH$_3$O), 6.3 (CH), 7.9 (NH), 13.8 (NH), ppm indicating the title compound.

EXAMPLE 5

Methyl 2-[[(4,6-Dimethoxy-1,3,5-triazin-2-yl)aminocarbonyl]aminosulfonyl]-1-cyclopentene-1-carboxylate The sulfonyl isocyanate product of Example 3 (5 g) was diluted to a concentration of 1.5M with dry acetonitrile and 2.0 ml of this solution was added to a stirred suspension of 0.27 g 4,6-dimethoxy-1,3,5-triazine-2-amine in 4.0 ml dry acetonitrile under a nitrogen atmosphere. The mixture was heated briefly on the steam bath until a homogeneous solution resulted, then stirred at ambient temperature for 24 hours. Dilution of the mixture with ether precipitated the product which was collected by filtration and dried to 0.54 g of white crystalline solid; m.p. 168°–169°. An infrared spectrum (nujol) exhibited absorptions at 1730 and 1700 cm$^{-1}$ and an NMR (60 MHz) spectrum in CDCl$_3$/DMSO-d$_6$ solution exhibited absorptions at 2.1 (CH$_2$), 3.0 (CH$_2$×2), 3.75 (CH$_3$O), 4.0 (CH$_3$O×2), 9.9 (NH), 12.3 (NH) ppm indicating the title compound.

By application of Examples 1 through 5 and/or the processes described above, the compounds of Tables I through VII may be prepared.

TABLE I-continued

[Structure: cycloalkene ring with (CH$_2$)$_n$, R substituent, SO$_2$NHC(O)N(R$_3$)- linked to pyrimidine/triazine with X, Y, Z substituents]

| R | n | R$_3$ | X | Y | Z | m.p. (°C.) |
|---|---|---|---|---|---|---|
| C(O)N(pyrrolidinyl) | 4 | CH$_3$ | OCH$_3$ | CH$_3$ | N | |
| SCH$_3$ | 3 | H | OCH$_3$ | OCH$_3$ | CH | |
| SC$_2$H$_5$ | 4 | H | OCH$_3$ | OCH$_3$ | N | |
| S(CH$_2$)$_3$H | 3 | H | CH$_3$ | CH$_3$ | CH | |
| S(CH$_2$)$_3$H | 4 | H | CH$_3$ | OCH$_3$ | CH | |
| S(O)C$_2$H$_5$ | 3 | H | CH$_3$ | CH$_3$ | N | |
| S(O)CH$_3$ | 3 | H | CH$_3$ | C$_2$H$_5$ | CH | |
| SO$_2$CH$_3$ | 4 | H | CH$_3$ | OCH$_3$ | CH | |
| SO$_2$CH$_3$ | 3 | H | OCH$_3$ | OCH$_3$ | CH | |
| SO$_2$CH$_3$ | 4 | H | CH$_3$ | OCH$_3$ | N | |
| SO$_2$CH$_3$ | 3 | H | CH$_3$ | CH$_3$ | CH | |
| SO$_2$C$_2$H$_5$ | 3 | H | OCH$_3$ | CH$_3$ | CH | |
| SO$_2$C$_2$H$_5$ | 4 | H | CH$_3$ | OCH$_3$ | N | |
| SO$_2$(CH$_2$)$_3$H | 3 | H | OCH$_3$ | OCH$_3$ | CH | |
| SO$_2$(CH$_2$)$_3$H | 4 | H | OCH$_3$ | OCH$_3$ | N | |
| CO$_2$CH$_3$ | 3 | H | CH$_3$ | CH(OCH$_3$)$_2$ | CH | |
| CO$_2$CH$_3$ | 3 | H | OCH$_3$ | CH(OCH$_2$CH$_2$O) | N | |
| CO$_2$CH$_3$ | 3 | H | CH$_3$ | CH(OCH$_2$CH$_2$O) | CH | |
| CO$_2$CH$_3$ | 4 | H | CH$_3$ | CH(OCH$_3$)$_2$ | N | |

TABLE II

[Structure: alkene with R$_1$, R, R$_2$, SO$_2$NHC(O)N(R$_3$)- linked to pyrimidine/triazine with X, Y, Z substituents]

| R | R$_1$ | R$_2$ | R$_3$ | X | Y | Z | m.p. (°C.) |
|---|---|---|---|---|---|---|---|
| F | F | F | H | OCH$_3$ | OCH$_3$ | CH | |
| Cl | Cl | Cl | H | OCH$_3$ | CH$_3$ | CH | 165–167° |
| Br | Br | Br | H | CH$_3$ | CH$_3$ | CH | |
| Br | Br | H | H | CH$_3$ | OCH$_3$ | N | |
| Cl | Cl | H | H | OCH$_3$ | OCH$_3$ | N | |
| CH$_3$ | CH$_3$ | H | H | OCH$_3$ | OCH$_3$ | CH | |
| C$_2$H$_5$ | Cl | H | H | CH$_3$ | OCH$_3$ | CH | |
| (CH$_2$)$_3$H | H | CH$_3$ | H | CH$_3$ | OCH$_3$ | N | |
| CH$_3$ | CH$_3$ | H | H | OCH$_3$ | OCH$_3$ | N | |
| C$_2$H$_5$ | H | (CH$_2$)$_3$H | H | CH$_3$ | OCH$_3$ | CH | |
| CH(CH$_3$)$_2$ | H | C$_2$H$_5$ | H | CH$_3$ | OCH$_3$ | N | |
| CH$_3$ | CH$_3$ | H | H | CH$_3$ | CH$_3$ | CH | |
| Cl | CH$_3$ | H | H | CH$_3$ | CH$_3$ | N | |
| CH$_3$ | Cl | H | CH$_3$ | CH$_3$ | OCH$_3$ | CH | |
| CH$_3$ | (CH$_2$)$_3$H | H | H | CH$_3$ | CH$_3$ | CH | |
| CO$_2$CH$_3$ | CH$_3$ | H | H | CH$_3$ | CH$_3$ | CH | |
| CO$_2$CH$_3$ | H | CH$_3$ | H | CH$_3$ | OCH$_3$ | CH | |
| CO$_2$CH$_3$ | H | CH$_3$ | H | CH$_3$ | CH$_3$ | CH | |
| CO$_2$CH$_3$ | C$_2$H$_5$ | H | H | OCH$_3$ | OCH$_3$ | CH | |
| CO$_2$CH$_3$ | H | C$_2$H$_5$ | H | OCH$_3$ | OCH$_3$ | N | |
| CO$_2$CH$_3$ | CH$_3$ | H | H | OCH$_3$ | CH$_3$ | N | |
| CO$_2$CH$_3$ | CH$_3$ | CH$_3$ | H | OCH$_3$ | CH$_3$ | N | |
| CO$_2$CH$_3$ | Br | H | H | OCH$_3$ | OCH$_3$ | CH | |
| CO$_2$CH$_3$ | Cl | Cl | H | OCH$_3$ | OCH$_3$ | N | |
| CO$_2$C$_2$H$_5$ | H | CH$_3$ | H | CH$_3$ | CH$_3$ | CH | |
| CO(CH$_2$)$_4$H | H | Cl | H | CH$_3$ | CH$_3$ | N | |
| C(O)SCH$_3$ | H | CH$_3$ | H | CH$_3$ | OCH$_3$ | CH | |
| Cl | Cl | Cl | H | CH$_3$ | CH$_3$ | CH | 157–160° |
| Cl | Cl | Cl | H | OCH$_3$ | OCH$_3$ | CH | 178–179° |
| Cl | Cl | Cl | H | OCH$_3$ | CH$_3$ | N | 140–141° |
| Cl | Cl | Cl | H | OCH$_3$ | OCH$_3$ | N | 153–155° |
| C(O)N(CH$_3$)$_2$ | H | CH$_3$ | H | CH$_3$ | OCH$_3$ | N | |

TABLE I

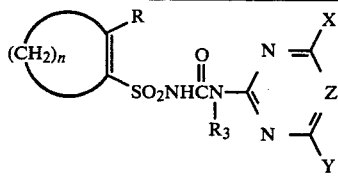

| R | n | R₃ | X | Y | Z | m.p. (°C.) |
|---|---|---|---|---|---|---|
| F | 4 | H | CH₃ | CH₃ | CH | |
| Cl | 4 | H | CH₃ | OCH₃ | N | |
| Cl | 4 | H | OCH₃ | OCH₃ | CH | |
| Cl | 3 | H | CH₃ | OCH₃ | CH | |
| Cl | 3 | H | OCH₃ | OCH₃ | CH | |
| Cl | 4 | H | OCH₃ | OCH₃ | N | |
| Br | 3 | H | CH₃ | CH₃ | CH | |
| Br | 4 | H | CH₃ | OCH₃ | CH | |
| CH₃ | 3 | H | CH₃ | OCH₃ | N | |
| (CH₂)₃H | 4 | H | CH₃ | OCH₃ | CH | |
| C₂H₅ | 4 | H | OCH₃ | OCH₃ | CH | |
| CH₃ | 4 | CH₃ | CH₃ | OCH₃ | CH | |
| CO₂CH₃ | 3 | H | CH₃ | CH₃ | CH | 189–191° |
| CO₂CH₃ | 3 | H | CH₃ | OCH₃ | CH | 161–163° |
| CO₂CH₃ | 3 | H | OCH₃ | OCH₃ | CH | 177–179° |
| CO₂CH₃ | 3 | H | OCH₃ | OCH₃ | N | 168–169° |
| CO₂CH₃ | 3 | H | CH₃ | OCH₃ | N | 158–160° |
| CO₂CH₃ | 3 | H | CH₃ | CH₃ | N | 121–133° |
| CO₂CH₃ | 4 | H | CH₃ | CH₃ | CH | |
| CO₂CH₃ | 4 | H | CH₃ | OCH₃ | CH | |
| CO₂CH₃ | 4 | H | OCH₃ | OCH₃ | CH | |
| CO₂CH₃ | 4 | H | CH₃ | CH₃ | N | |
| CO₂CH₃ | 4 | H | CH₃ | OCH₃ | N | |
| CO₂CH₃ | 4 | H | OCH₃ | OCH₃ | N | |
| CO₂CH₃ | 3 | H | Cl | OCH₃ | CH | |
| CO₂CH₃ | 4 | H | Cl | NH₂ | CH | |
| CO₂CH₃ | 3 | H | Cl | NHCH₃ | CH | |
| CO₂CH₃ | 4 | H | Cl | N(CH₃)₂ | CH | |
| CO₂CH₃ | 3 | CH₃ | CH₃ | C₂H₅ | CH | |
| CO₂CH₃ | 4 | H | OCH₃ | C₂H₅ | N | |
| CO₂CH₃ | 3 | H | CH₃ | CH₂OCH₃ | CH | |
| CO₂CH₃ | 4 | H | OCH₃ | N(CH₃)₂ | CH | |
| CO₂CH₃ | 3 | H | CH₃ | OC₂H₅ | N | |
| CO₂C₂H₅ | 3 | H | CH₃ | CH₃ | CH | |
| CO₂C₂H₅ | 4 | H | CH₃ | OCH₃ | CH | |
| CO₂CH(CH₃)₂ | 4 | H | OCH₃ | OCH₃ | N | |
| CO₂(CH₂)₃CH₃ | 3 | H | OCH₃ | CH₃ | N | |
| CO₂CH₂CH₂OCH₃ | 3 | H | CH₃ | OCH₃ | CH | |
| CH₂CH₂Cl | 4 | H | OCH₃ | CH₃ | N | |
| CH₂CH=CH₂ | 4 | H | CH₃ | OCH₃ | CH | |
| CH₂CH=CH₂ | 3 | H | CH₃ | CH₃ | CH | |
| C(O)SCH₃ | 3 | H | OCH₃ | CH₃ | CH | |
| C(O)SCH₃ | 4 | H | CH₃ | CH₃ | CH | |
| C(O)SC₂H₅ | 3 | H | OCH₃ | OCH₃ | N | |
| C(O)S(CH₂)₄H | 3 | H | CH₃ | OCH₃ | CH | |
| C(O)N(CH₃)₂ | 4 | H | CH₃ | CH₃ | N | |
| C(O)NHCH₃ | 4 | H | CH₃ | OCH₃ | N | |
| C(O)N(CH₃)(CH₂)₃H | 3 | H | CH₃ | OCH₃ | CH | |
| C(O)N(C₂H₅)₂ | 3 | H | OCH₃ | OCH₃ | CH | |
| C(O)N(CH₃)₂ | 4 | H | OCH₃ | OCH₃ | CH | |
| 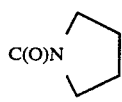 | 3 | H | CH₃ | CH₃ | CH | |
| 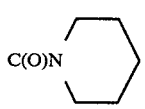 | 4 | H | CH₃ | OCH₃ | CH | |
| 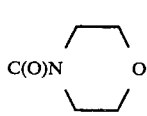 | 3 | H | OCH₃ | OCH₃ | CH | |

TABLE II-continued

Structure: R1, R substituents on alkene with R2, SO2NHC(O)N(R3)C(=N-)- connected to a triazine/pyrimidine ring with X, Y, Z substituents

| R | R₁ | R₂ | R₃ | X | Y | Z | m.p. (°C.) |
|---|---|---|---|---|---|---|---|
| C(O)N(pyrrolidine) | H | CH₃ | H | OCH₃ | OCH₃ | CH | |
| C(O)N(C₂H₅)₂ | C₂H₅ | H | H | OCH₃ | CH₃ | CH | |
| SCH₃ | CH₃ | CH₃ | H | Cl | OCH₃ | CH | |
| SC₂H₅ | H | C₂H₅ | H | CH₃ | N(CH₃)₂ | CH | |
| S(O)(CH₂)₃H | H | CH₃ | H | CH₃ | OCH₃ | N | |
| S(O)CH₃ | H | CH₃ | H | OCH₃ | OCH₃ | CH | |
| SO₂CH₃ | H | Cl | H | CH₃ | CH₃ | CH | |
| SO₂(CH₂)₃H | H | Cl | H | CH₃ | OCH₃ | N | |
| SO₂CH₃ | Cl | Cl | H | OCH₃ | OCH₃ | N | |

TABLE III

| R | R₃ | n | p | X₁ | Q | m.p. (°C.) |
|---|---|---|---|---|---|---|
| Cl | H | 3 | 2 | CH₃ | O | |
| Cl | H | 4 | 3 | OCH₃ | O | |
| Cl | H | 3 | 3 | CH₃ | O | |
| F | H | 4 | 2 | CH₃ | CH₂ | |
| Br | H | 4 | 3 | OCH₃ | O | |
| CH₃ | H | 3 | 3 | CH₃ | O | |
| C₂H₅ | H | 3 | 2 | OC₂H₅ | O | |
| CH₃ | CH₃ | 4 | 2 | CH₃ | CH₂ | |
| CO₂CH₃ | H | 4 | 3 | CH₃ | O | |
| CO₂CH₃ | H | 3 | 2 | OCH₃ | O | |
| CO₂CH₃ | H | 3 | 3 | CH₃ | O | |
| CO₂CH₃ | H | 4 | 2 | CH₃ | CH₂ | |
| CO₂CH₃ | H | 4 | 3 | Cl | O | |
| CO₂CH₃ | H | 3 | 2 | H | O | |
| CO₂C₂H₅ | H | 3 | 3 | CH₃ | O | |
| C(O)N(CH₃)₂ | H | 3 | 2 | CH₃ | O | |
| C(O)N(pyrrolidine) | H | 4 | 2 | CH₃ | CH₂ | |
| SCH₃ | H | 4 | 3 | CH₃ | O | |
| SO₂CH₃ | H | 3 | 3 | OCH₃ | O | |
| S(O)C₂H₅ | H | 3 | 2 | CH₃ | O | |
| SO₂C₂H₅ | H | 4 | 2 | OCH₃ | CH₂ | |
| C(O)SCH₃ | H | 3 | 2 | CH₃ | O | |

TABLE IV

| R | n | R₃ | X₂ | m.p. (°C.) |
|---|---|---|---|---|
| Cl | 2 | H | CH₃ | |

TABLE IV-continued

| R | n | R₃ | X₂ | m.p. (°C.) |
|---|---|---|---|---|
| Cl | 2 | H | C₂H₅ | |
| Cl | 3 | H | CH₃ | |
| Br | 3 | H | OCH₃ | |
| F | 2 | H | OC₂H₅ | |
| CH₃ | 2 | H | CH₃ | |
| C₂H₅ | 3 | H | OCH₃ | |
| CH₃ | 3 | H | CH₃ | |
| CO₂CH₃ | 2 | H | CH₃ | |
| CO₂CH₃ | 2 | H | OCH₃ | |
| CO₂CH₃ | 3 | H | CH₃ | |
| CO₂CH₃ | 3 | H | OCH₃ | |
| CO₂CH₃ | 2 | CH₃ | CH₃ | |
| CO₂CH₃ | 3 | H | CH₃ | |
| CO₂C₂H₅ | 2 | H | CH₃ | |
| C(O)N(CH₃)₂ | 2 | H | OCH₃ | |
| C(O)N(pyrrolidine) | 3 | H | CH₃ | |
| C(O)SCH₃ | 3 | H | CH₃ | |
| SCH₃ | 2 | H | OCH₃ | |
| SO₂CH₃ | 2 | H | CH₃ | |
| S(O)CH₃ | 3 | H | OCH₃ | |
| SO₂C₂H₅ | 3 | H | CH₃ | |

TABLE V

| R | n | R₃ | X₃ | Y₁ | m.p. (°C.) |
|---|---|---|---|---|---|
| Cl | 3 | H | CH₃ | CH₃ | |
| Cl | 2 | H | OCH₃ | CH₃ | |

TABLE V-continued

| R | n | $R_3$ | $X_3$ | $Y_1$ | m.p. (°C.) |
|---|---|---|---|---|---|
| Cl | 3 | H | $CH_3$ | $OCH_3$ | |
| Br | 2 | H | $CH_3$ | $CH_3$ | |
| F | 3 | H | $CH_3$ | $OCH_3$ | |
| $CH_3$ | 2 | H | $OCH_3$ | $CH_3$ | |
| $C_2H_5$ | 3 | H | $CH_3$ | $CH_3$ | |
| $CH_3$ | 3 | H | $OCH_3$ | $CH_3$ | |
| $CO_2CH_3$ | 3 | H | $OCH_3$ | $OCH_3$ | |
| $CO_2CH_3$ | 3 | H | $CH_3$ | $OCH_3$ | |
| $CO_2CH_3$ | 2 | H | $OCH_3$ | $CH_3$ | |
| $CO_2CH_3$ | 2 | H | $CH_3$ | $CH_3$ | |
| $CO_2CH_3$ | 3 | $CH_3$ | $CH_3$ | $CH_3$ | |
| $CO_2CH_3$ | 2 | H | $OCH_3$ | $CH_3$ | |
| $CO_2C_2H_5$ | 3 | H | $CH_3$ | $OCH_3$ | |
| $C(O)N(CH_3)_2$ | 2 | H | $CH_3$ | $CH_3$ | |
| C(O)N⟨(pyrrolidinyl)⟩ | 2 | H | $CH_3$ | $OCH_3$ | |
| $C(O)SCH_3$ | 3 | H | $OCH_3$ | $CH_3$ | |
| $SCH_3$ | 3 | H | $CH_3$ | $CH_3$ | |
| $SO_2CH_3$ | 2 | H | $CH_3$ | $CH_3$ | |
| $S(O)CH_3$ | 2 | H | $OCH_3$ | $CH_3$ | |
| $SO_2C_2H_5$ | 3 | H | $OCH_3$ | $CH_3$ | |

TABLE VI

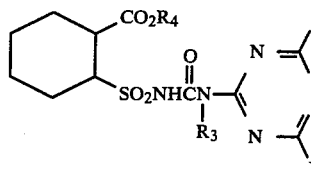

| $R_4$ | $R_3$ | X | Y | Z | m.p. (°C.) |
|---|---|---|---|---|---|
| $CH_3$ | H | $CH_3$ | $CH_3$ | CH | 170–171° |
| $CH_3$ | H | $CH_3$ | $OCH_3$ | CH | 185–186° |
| $CH_3$ | H | $OCH_3$ | $OCH_3$ | CH | 177–178° |
| $CH_3$ | H | $CH_3$ | $OCH_3$ | N | 147–149° |
| $CH_3$ | H | $OCH_3$ | $OCH_3$ | N | 152–154° |
| $CH_3$ | H | Cl | $OCH_3$ | CH | |
| $CH_3$ | $CH_3$ | $CH_3$ | $OCH_3$ | CH | |
| $C_2H_5$ | H | $OCH_3$ | $OCH_3$ | N | |
| $CH(CH_3)_2$ | H | $CH_3$ | $OCH_3$ | N | |
| $CH(CH_3)C_2H_5$ | H | $CH_3$ | $OCH_3$ | CH | |
| $CH_2CH_2Cl$ | H | $OCH_3$ | $OCH_3$ | CH | |
| $CH_2CH_2OCH_3$ | H | $OCH_3$ | $CH_2OCH_3$ | CH | |
| $CH_2CH{=}CH_2$ | H | $CH_3$ | $CH(OCH_3)_2$ | CH | |

TABLE VII

| $R_4$ | $R_3$ | X | Y | Z | m.p. (°C.) |
|---|---|---|---|---|---|
| $CH_3$ | H | $CH_3$ | $CH_3$ | CH | |
| $CH_3$ | H | $CH_3$ | $OCH_3$ | CH | 151–153° |

TABLE VII-continued

| $R_4$ | $R_3$ | X | Y | Z | m.p. (°C.) |
|---|---|---|---|---|---|
| $CH_3$ | H | $OCH_3$ | $OCH_3$ | CH | 152–154° |
| $CH_3$ | H | $OCH_3$ | $CH_3$ | N | 168–170° |
| $CH_3$ | H | $OCH_3$ | $OCH_3$ | N | 172–175° |
| $CH_3$ | H | Cl | $OCH_3$ | CH | |
| $CH_3$ | $CH_3$ | $CH_3$ | $OCH_3$ | CH | |
| $CH_3$ | H | $OCH_3$ | $NHCH_3$ | CH | |
| $C_2H_5$ | H | $CH_3$ | $OCH_3$ | N | |
| $CH(CH_3)_2$ | H | $CH_3$ | $OCH_3$ | CH | |
| $CH(CH_3)C_2H_5$ | H | $OCH_3$ | $OCH_3$ | N | |
| $CH_2CH_2Cl$ | H | $OCH_3$ | $CH_3$ | CH | |
| $CH_2CH_2OCH_3$ | H | $CH_3$ | $CH_2OCH_3$ | CH | |
| $CH_2CH{=}CH_2$ | H | $CH_3$ | $CH(OCH_3)_2$ | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE VIII

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 6

| Wettable Powder | |
|---|---|
| 2-[[(4,6-dimethylpyrimidin-2-yl)aminocarbonyl]aminosulfonyl]-1-cyclopentene-1-carboxylic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 7

| Wettable Powder | |
|---|---|
| 2-[[(4-methoxy-6-methylpyrimidin-2-yl)aminocarbonyl]-aminosulfonyl]-1-cyclopentene-1-carboxylic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 8

| Granule | |
|---|---|
| Wettable Powder of Example 7 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 9

| Extruded Pellet | |
|---|---|
| 2-[[(4,6-dimethyl-1,3,5-triazin-2-yl)aminocarbonyl]-aminosulfonyl]-1-cyclopentene-1-carboxylic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 10

| Oil Suspension | |
|---|---|
| 2-[[(4,6-dimethoxypyrimidin-2-yl)aminocarbonyl]aminosulfonyl]-1-cyclopentene-1-carboxylic acid, methyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 11

| Wettable Powder | |
|---|---|
| 2-[[(4-methoxy-6-methyl-1,3,5-triazin-2-yl)aminocarbonyl]aminosulfonyl]-1-cyclopentene-1-carboxylic acid, methyl ester | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 12

| Low Strength Granule | |
| --- | --- |
| 2-[[(4,6-dimethyl-1,3,5-triazin-2-yl)aminocarbonyl]-aminosulfonyl]-1-cyclopentene-1-carboxylic acid, methyl ester | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 13

| Aqueous Suspension | |
| --- | --- |
| 2-[[(4,6-dimethoxy-1,3,5-triazin-2-yl)aminocarbonyl]-aminosulfonyl]-1-cyclopentene-1-carboxylic acid, methyl ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 14

| Solution | |
| --- | --- |
| 2-[[(4,6-dimethylpyrimidin-2-yl)aminocarbonyl]-aminosulfonyl]-1-cyclopentene-1-carboxylic acid, methyl ester, sodium salt | 5% |
| water | 95% |

The salt is added directly to the water with stirring to produce the solution, which may then be packaged for use.

EXAMPLE 15

| Low Strength Granule | |
| --- | --- |
| 2-[[(4,6-dimethyl-1,3,5-triazin-2-yl)aminocarbonyl]-aminosulfonyl]-1-cyclopentene-1-carboxylic acid, methyl ester | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 16

| Granule | |
| --- | --- |
| 2-[[(4-methoxy-6-methylpyrimidin-2-yl)aminocarbonyl]- | 80% |
| aminosulfonyl]-1-cyclopentene-1-carboxylic acid, methyl ester | |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 17

| High Strength Concentrate | |
| --- | --- |
| 2-[[(4,6-dimethoxypyrimidin-2-yl)aminocarbonyl]aminosulfonyl]-1-cyclopentene-1-carboxylic acid, methyl ester | 99% |
| silica aerogel | 0.5% |
| synthetic amorphous silica | 0.5% |

The ingredients are blended and ground in a hammermill to produce a material essentially all passing a U.S.S. No. 50 screen (0.3 mm opening). The concentrate may be formulated further if necessary.

EXAMPLE 18

| Wettable Powder | |
| --- | --- |
| 2-[[(4,6-dimethoxy-1,3,5-triazin-2-yl)aminocarbonyl]aminosulfonyl]-1-cyclopentene-1-carboxylic acid, methyl ester | 90% |
| dioctyl sodium sulfosuccinate | 0.1% |
| synthetic fine silica | 9.9% |

The ingredients are blended and ground in a hammermill to produce particles essentially all below 100 microns. The material is sifted through a U.S.S. No. 50 screen and then packaged.

EXAMPLE 19

| Wettable Powder | |
| --- | --- |
| 2-[[(4-methoxy-6-methyl-1,3,5-triazin-2-yl)aminocarbonyl]aminosulfonyl]-1-cyclopentene-1-carboxylic acid, methyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 20

| Oil Suspension | |
|---|---|
| 2-[[(4,6-dimethylpyrimidin-2-yl)aminocarbonyl]amino-sulfonyl]-1-cyclopentene-1-carboxylic acid, methyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 21

| Dust | |
|---|---|
| 2-[[(4-methoxy-6-methylpyrimidin-2-yl)aminocarbonyl]-aminosulfonyl]-1-cyclopentene-1-carboxylic acid, methyl ester | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

The compounds of the present invention are powerful herbicides. They have utility for broadspectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for plant growth modification, such as defoliation and growth retardation.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.06 to 10 kg/ha, the lower rates being suggested for use on lighter soils and/or those having a low organic matter content, for plant growth modification or for situations, where only short-term persistence is required.

The compounds of the invention may be used in combination with any other commercial herbicide examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (Digitaria sp.), barnyardgrass (Echinochloa crusgalli), wild oats (Avena fatua), cassia (Cassia tora), morningglory (Ipomoea sp.), cocklebur (Xanthium sp.), sorghum, corn, soybean, sugarbeet, rice, wheat and nutsedge tubers (Cyperus rotundus) were planted in a growth medium and treated pre-emergence with the chemicals dissolved in a non-phytotoxic solvent. At the same time, cotton having five leaves (including cotyledonary ones), bush beans with the third trifoliolate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, sugarbeets with two leaves, and nutsedge with three to five leaves were sprayed. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following meanings:

C=chlorosis/necrosis;
D=defoliation;
E=emergence inhibition;
G=growth retardation;
H=formative effects;
S=albinism; and
U=unusual pigmentation;
6Y=abscised buds or flowers.

The ratings for the compounds tested by this procedure are presented in Table A. It will be seen that certain of the compounds tested are highly active pre- and/or post-emergence herbicides and/or possess plant growth modifying properties.

Table Structures

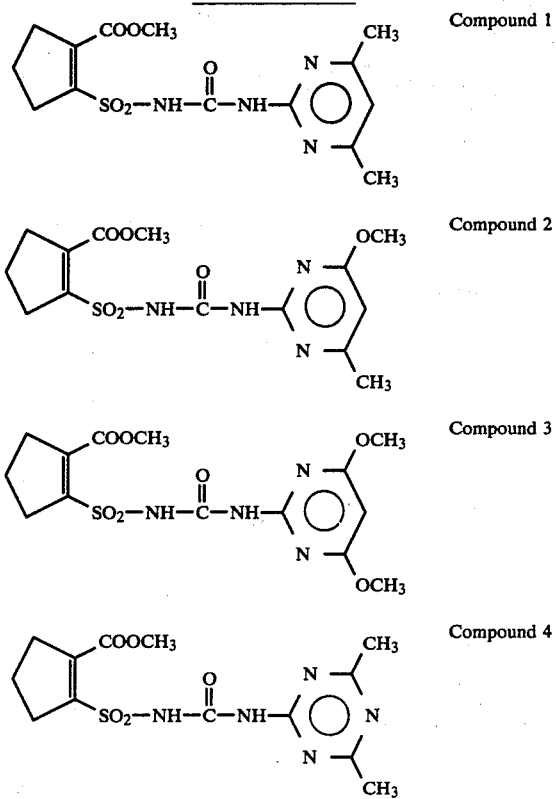

-continued
Table Structures
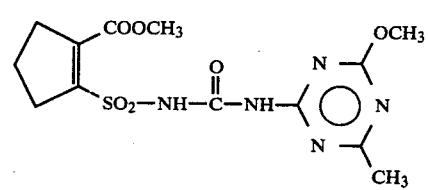 Compound 5
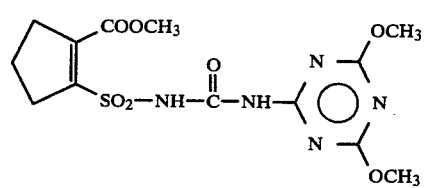 Compound 6
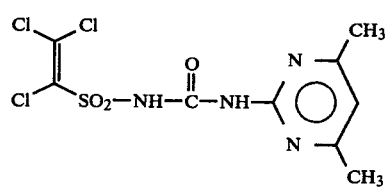 Compound 7
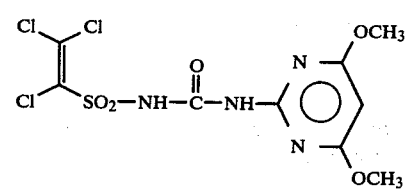 Compound 8
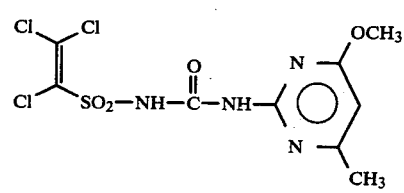 Compound 9
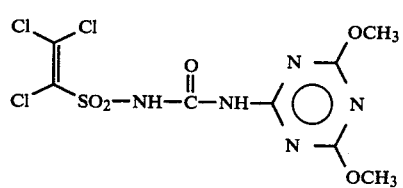 Compound 10
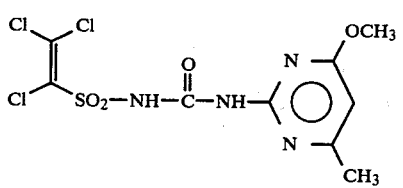 Compound 11
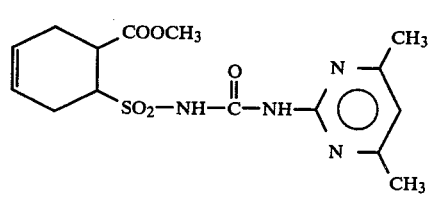 Compound 12
-continued
Table Structures
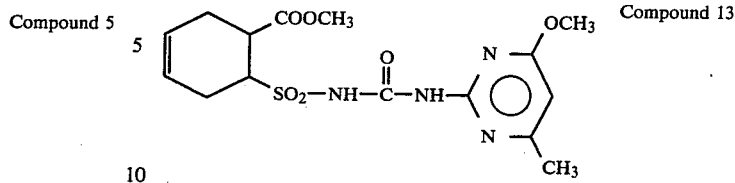 Compound 13
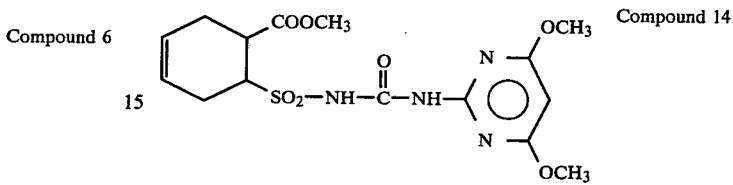 Compound 14
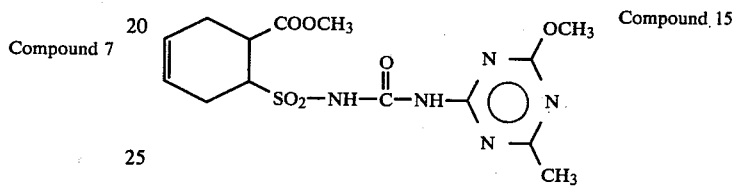 Compound 15
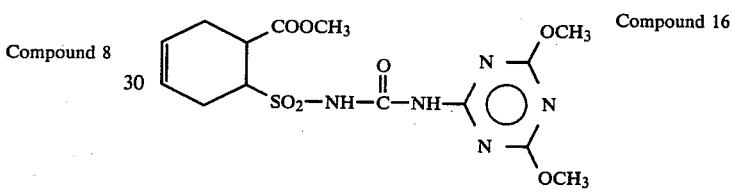 Compound 16
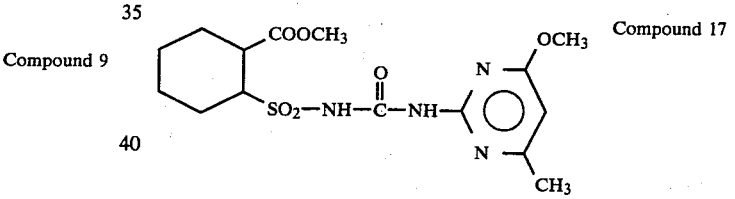 Compound 17
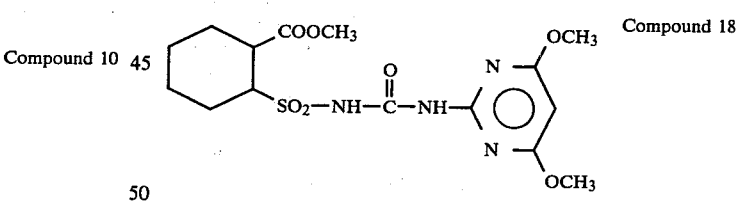 Compound 18
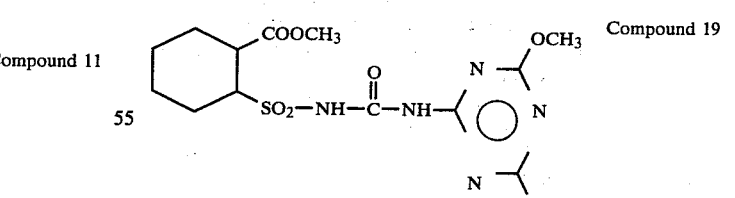 Compound 19
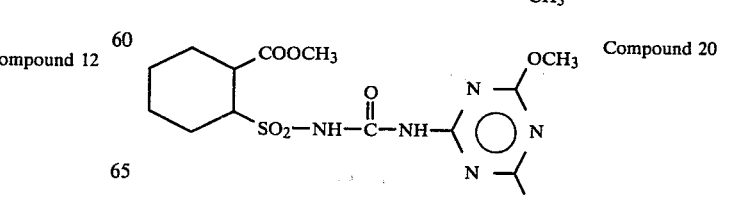 Compound 20

TABLE A

| | Compound 1 | Cmpd. 2 | Cmpd. 3 | Cmpd. 4 | | Compound 5 | Cmpd. 6 | Cmpd. 7 |
|---|---|---|---|---|---|---|---|---|
| Rate kg/ha | 0.4 | .05 | .05 | .05 | .05 | 0.4 | .05 | .05 |
| | | | POST EMERGENCE | | | | | |
| Bush bean | 9D,9G,6Y | 6D,8G,6Y | 7D,8G,6Y | 6D,6G,6Y | 4C,9G,6Y | 9C | 9D,9C,6Y | 3C,7G,6Y | 0
| Cotton | 4C,9G | 1C,6G | 2C,7G | 1C,6G | 5G | 4C,9G | 3C,8G | 1C,5G | 0
| Morningglory | 3C,8G | 2C,6G | 2C,5G | 2C,7G | 3G | 3C,8G | 1C,4G | 2C,5G | 0
| Cocklebur | 9C | 3C,9H | 2C,9H | 5C,9G | 0 | 10C | 2C,6G | 1C,5H | 0
| Cassia | 2C,5G | 2C,5G | 1C,4G | 2C,4G | 0 | 3C,8H | 3C | 1C | 0
| Nutsedge | 9C | 3C,9G | 3C,9G | 3C,9G | 2G | 5C,9G | 0 | 1C,3G | 0
| Crabgrass | 9C | 2C,8G | 2C,9H | 2C,9G | 0 | 7C,9G | 2G | 1C | 0
| Barnyardgrass | 10C | 9C | 9C | 9C | 0 | 9C | 3C,9H | 3C,9H | 0
| Wild Oats | 9C | 3C,9H | 2C,9H | 3C,9G | 0 | 3C,9G | 0 | 2C | 0
| Wheat | 5C,9G | 1C,6G | 3C,9H | 3C,9G | 0 | 6C,9G | 1C | 2C,5G | 0
| Corn | 5U,9C | 1U,9G | 2C,9G | 2U,9G | 2C,8H | 6C,9G | 2U,9G | 5C,9G | 0
| Soybean | 4C,9G | 2C,5H | 2C,7H | 3C,7H | 1C,5H | 6C,9H | 1C,8H | 2C,9G,5X | 0
| Rice | 6C,9G | 2C,9G | 4C,9G | 5C,9G | 5G | 5C,9G | 4C,9G | 4C,9G | 0
| Sorghum | 9C | 3C,9G | 5C,9G | 8C,9G | 2C,9H | 5U,9G | 2C,9H | 3C,9G | 0
| Sugarbeet | — | — | — | — | — | — | — | — | — |

| | Compound 8 | Compound 9 | Cmpd. 10 | | Compound 11 | Cmpd. 12 | Compound 13 | Cmpd. 14 | Cmpd. 15 |
|---|---|---|---|---|---|---|---|---|---|
| Rate kg/ha | 0.4 | .05 | .05 | 2 | .05 | .05 | 2 | 0.4 | 0.4 | 2 | 0.4 | 0.4 |
| | | | POST-EMERGENCE | | | | | | |
| Bush bean | 2G | 2G | 1C | 2C,3G | 0 | 1C | 4C | 3C,6Y | 4C,6Y | 4S,5G,6Y | 4S,6G,6Y | 4C,8G,6Y |
| Cotton | 0 | 0 | 0 | 1C | 0 | 1C | 2C | 2C | 2C | 2C | 2C | 1C |
| Morningglory | 1C | 2H | 0 | 1C,3G | 0 | 0 | 2C | 1C | 1C | 2C | 2C,6H | 3C,5H |
| Cocklebur | 5C,9G | 2H | 1C | 4C,8G | 0 | 4G | 9C | 9C | 2C,8G | 10C | 2C,5G | 9C |
| Cassia | 0 | 0 | 0 | 1C | 0 | 1C | 2C | 1C | 1C | 2C,4G | 3C,5G | 2C |
| Nutsedge | 0 | 3C,5G | 0 | 3C,9G | 0 | 0 | 1C,4G | 0 | 0 | 5G | 0 | 3G |
| Crabgrass | 0 | 0 | 0 | 2C | 0 | 0 | 1C,4G | 0 | 0 | 4G | 2C | 0 |
| Barnyardgrass | 0 | 0 | 0 | 3C,8H | 0 | 0 | 3C,9H | 0 | 0 | 2C,6H | 2C | 0 |
| Wild Oats | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 |
| Corn | 0 | 0 | 1H | 9H | 0 | 3H | 2C,8H | 2C,2H | 0 | 0 | 0 | 2G |
| Soybean | 0 | 0 | 0 | 1H | 0 | 0 | 1C | 1C,1H | 1C,2H | 2C,5H | 2H | 1H |
| Rice | 0 | 0 | 0 | 2C,7G | 0 | 0 | 2C,6G | 1C | 0 | 1C,5G | 5G | 0 |
| Sorghum | 0 | 0 | 0 | 3C,8H | 0 | 2G | 3C,9G | 1C,3G | 1C,3G | 2C,9H | 4G | 0 |
| Sugarbeet | — | — | — | — | — | — | — | — | — | — | — | — |

| | Cmpd. 16 | Cmpd. 17 | Cmpd. 18 | Cmpd. 19 | Compound 20 | |
|---|---|---|---|---|---|---|
| Rate kg/ha | 0.4 | 0.4 | 0.4 | 0.4 | 2 | |
| | | POST-EMERGENCE | | | | |
| Bush bean | 3C,9G,6Y | 1H | 3C,6G,6Y | 3C,5G,6Y | 2C,2H | 5C,3H,6Y |
| Cotton | 2C,3H | 1B | 2C,2H | 2C,3G | 2C | 1C |
| Morningglory | 2C,3H | 2C | 3C,7H | 3C,8H | 3C,5H | 3C,5H |
| Cocklebur | 2H | 0 | 1C | 3C,4G | 0 | 0 |
| Cassia | 2C | 1C | 2C | 2C | 1C | 3C |
| Nutsedge | 0 | 0 | 1C,4G | 0 | 0 | 0 |
| Crabgrass | 1C | 0 | 0 | 0 | 0 | 0 |
| Barnyardgrass | 1C,2H | 0 | 2C,5H | 0 | 0 | 1C,3H |
| Wild Oats | 0 | 0 | 0 | 0 | 0 | 0 |
| Wheat | 0 | 0 | 0 | 0 | 0 | 0 |
| Corn | 0 | 0 | 2G | 2C | 0 | 0 |
| Soybean | 1C | 1C | 3C,2H | 2C,2H | 4C,4G | 3C |
| Rice | 0 | 0 | 2C,5G | 1C,3G | 3G | 0 |
| Sorghum | 0 | 0 | 2C,5G | 0 | 2G | 2C |
| Sugarbeet | — | 1C | 2C,3H | 4C,8G | 3C,7G | 3C,6G |

| | Compound 1 | Cmpd. 2 | Cmpd. 3 | Cmpd. 4 | | Compound 5 | Cmpd. 6 | Cmpd. 7 |
|---|---|---|---|---|---|---|---|---|
| Rate kg/ha | 0.4 | .05 | .05 | .05 | .05 | 0.4 | .05 | .05 |
| | | | PRE-EMERGENCE | | | | | |
| Morningglory | 6G | 1C,6G | 1C,6G | 3C,6G | 0 | 3C,7G | 1C,4G | 2C,5H | 0 |
| Cocklebur | 9H | 2C,9H | 9H | 2C,9H | 0 | 9H | 9C | 9H | 3H |
| Cassia | 2C,8G | 1C,5G | 2C,8G | 3C,8G | 0 | 3C,9G | 2C,8G | 2C,7G | 0 |
| Nutsedge | 10E | 2C,9G | 9G | 10E | 0 | 2C,6G | 2G | 6G | 0 |
| Crabgrass | 2C,6G | 1C | 2C,6G | 3C,7G | 0 | 2C,5G | 1C | 0 | 0 |
| Barnyardgrass | 3C,9H | 3C,9H | 5C,9H | 5C,9H | 0 | 5C,9H | 1C | 2C,6H | 0 |
| Wild Oats | 5C,9H | 2C,9G | 5C,9G | 3C,9G | 0 | 3C,9G | 1C,4G | 0 | 0 |
| Wheat | 3C,9H | 1C,9H | 9H | 2C,9G | 0 | 1C,9G | 1C | 0 | 0 |
| Corn | 10H | 2C,9H | 5C,9H | 2C,9H | 2C,7G | 9H | 3C,9H | 3C,9H | 0 |
| Soybean | 6H | 2C,5H | 3C,7H | 3C,6H | 0 | 9H | 3C,8H | 2C,7H | 0 |
| Rice | 10E | 2C,8H | 10E | 10E | 2C,7G | 10E | 3C,9H | 5C,9H | 0 |
| Sorghum | 5C,9H | 7C,9H | 8C,9H | 2C,9H | 3C,8H | 6C,9H | 3C,9H | 3C,9H | 0 |
| Sugarbeet | — | — | — | — | — | — | — | — | — |

| | Compound 8 | Compound 9 | Cmpd. 10 | | Compound 11 | Cmpd. 12 | Compound 13 | Cmpd. 14 | Cmpd. 15 |
|---|---|---|---|---|---|---|---|---|---|
| Rate kg/ha | 0.4 | .05 | .05 | 2 | .05 | .05 | 2 | 0.4 | 0.4 | 2 | 0.4 | 0.4 |
| | | | PRE-EMERGENCE | | | | | | |
| Morningglory | 1H | 0 | 0 | 8G | 0 | 2C,6H | 8G | 1C | 2G | 2C,7G | 1C | 1C,1H |
| Cocklebur | 6G | 4G | 0 | 8H | 0 | 7H | 9H | 9H | 8H | 9H | 8H | 8H |

TABLE A-continued

| | | | | | | | | | | | | |
|---|---|---|---|---|---|---|---|---|---|---|---|---|
| Cassia | 8G | 0 | 0 | 2G | 0 | 6G | — | 3G | 4G | 5H | 2C | 0 |
| Nutsedge | 0 | 0 | 0 | 8G | 0 | 0 | 7G | 0 | 0 | 0 | 7G | 0 |
| Crabgrass | 0 | 0 | 0 | 2G | 0 | 3G | 5G | 0 | 0 | 0 | 1C | 2C |
| Barnyardgrass | 0 | 0 | 0 | 2C,8G | 0 | 2G | 5G | 2C | 1C | 3C,5H | 2C | 1C |
| Wild Oats | 0 | 0 | 0 | 0 | 0 | 0 | 0 | 0 | 0 | 2C,6G | 0 | 0 |
| Wheat | 0 | 0 | 0 | 3G | 0 | 0 | 3G | 0 | 0 | 2C,7G | 0 | 0 |
| Corn | 0 | 0 | 2C | 9G | 0 | 1C,3G | 2C,9G | 1C,3G | 1C,3G | 2C,7H | 1C,4G | 0 |
| Soybean | 0 | 0 | 0 | 0 | 0 | 0 | 1H | 1C | 2G | 1C,2H | 0 | 0 |
| Rice | 0 | 0 | 0 | 8H | 0 | 0 | 2G | 0 | 2G | 2C,8H | 0 | 0 |
| Sorghum | 0 | 0 | 0 | 3C,8G | 0 | 0 | 2C,9G | 0 | 0 | 2C,8G | 0 | 0 |
| Sugarbeet | — | — | — | — | — | — | — | 0 | 0 | 2C,8G | 3G | 0 |

| | | Cmpd. 16 | Cmpd. 17 | Cmpd. 18 | Cmpd. 19 | Compound 20 | |
|---|---|---|---|---|---|---|---|
| | Rate kg/ha | 0.4 | 0.4 | 0.4 | 0.4 | 0.4 | 2 |
| | | PRE-EMERGENCE | | | | | |
| | Morningglory | 1C | 2C | 2C,7G | 1C,4G | 3C,3H | 3C,6G |
| | Cocklebur | 8H | — | 8H | 0 | — | 7H |
| | Cassia | 0 | 2H | 2C,5H | 0 | 2C | 1C |
| | Nutsedge | 0 | 0 | 10E | 0 | 0 | 0 |
| | Crabgrass | 0 | 0 | 2G | 0 | 0 | 0 |
| | Barnyardgrass | 0 | 0 | 2C | 0 | 0 | 0 |
| | Wild Oats | 0 | 0 | 2C | 0 | 0 | 0 |
| | Wheat | 0 | 0 | 0 | 0 | 0 | 0 |
| | Corn | 0 | 0 | 2C,5G | 0 | 0 | 2C |
| | Soybean | 0 | 0 | 0 | 0 | 0 | 1C |
| | Rice | 0 | 0 | 0 | 0 | 0 | 1C |
| | Sorghum | 0 | 0 | 1C | 0 | 5G | 2G |
| | Sugarbeet | 0 | 5G | 0 | 0 | 7G | 0 |

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated preemergence with several test compounds within the scope of the invention.

Twenty-eight days after treatment, the plants were evaluated and visually rated for response to the chemical treatments utilizing the rating system described previously for Test A. The data are summarized in Table B. Note the high herbicidal activity of the compounds tested at the low rates of application selected for this evaluation.

TABLE B

| | PRE-EMERGENCE ON FALLSINGTON SILT LOAM | | | | | | | | | |
|---|---|---|---|---|---|---|---|---|---|---|
| | Compound 1 | | Compound 2 | | Compound 3 | | Compound 5 | | Compound 6 | |
| Rate kg/ha | 0.03 | 0.12 | 0.03 | 0.12 | 0.03 | 0.12 | 0.03 | 0.12 | 0.03 | 0.12 |
| Crabgrass | 4C | 7G | 6G | 8G | 6G | 7G | 0 | 5G | 2G | 3G |
| Barnyardgrass | 8G,5H | 9G,9C | 9G,9C | 10C | 8G,3H | 10C | 5G | 6G | 4G | 6G |
| Sorghum | — | — | — | — | — | — | 8G,3H | 9G,3H | 6G,3H | 8G,3H |
| Wild Oats | 6G | 7G,3H | 7G,3H | 7G,3H | 7G,3H | 7G,3H | 2G | 3G | 0 | 3G |
| Johnsongrass | 8G,5H | 8G,5H | 9G,5H | 9G,5H | 8G,3H | 8G,3H | 3G,2H | 5G,3H | 3G,2H | 5G,3H |
| Dallisgrass | 8G | 8G,3H | 9G | 9G,3H | 8G | 8G | 0 | 0 | 0 | 0 |
| Giant foxtail | 3G | 5G | 8G,3H | 9G,9C | 8G,5H | 9G,9C | 0 | 3G,3C | 2G | 5G,5C |
| Ky. bluegrass | 7G | 8G,8C | 10C | 10C | 10E | 10E | 2G | 10C | 7G,3H | 7G,5H |
| Cheatgrass | 7G,3H | 9G,9C | 10C | 10C | 10C | 10C | 3H | 5G,3H | 0 | 4G |
| Sugarbeets | 7G,5H | 9G,8C | 8G,8C | 9G,9C | 7G,5H | 8G,8C | 8G,8C | 9G,9C | 8G,7C | 9G,9C |
| Corn | 5G,2H | 8G,5H | 7G,5H | 8G,5H | 8G,5H | 10C | 5G,2H | 8G,5H | 4G | 7G,5H |
| Mustard | 8G | 9G,5C | 9G,8C | 10C | 9G,7C | 10C | 8G,3C | 9G,9C | 8G,3H | 9G,8C |
| Cocklebur | 4G | 5G | 6G | — | 5G | 7G,2C | 4G | 6G | 4G | 6G |
| Pigweed | 7G | 8G,8E | 10E | 10E | 10E | 10E | 10C | 10C | 9G,8C | 10E |
| Nutsedge | 6G | 10E | 8G | 10E | 10E | 10E | 0 | 4G | 4G | 5G |
| Cotton | 5G | 8G,5H | 8G,5H | 9G,5H | 6G | 8G,3H | 7G,3H | 8G,5H | 7G | 7G,3H |
| Morningglory | 3G,2C | 5G,2C | 4G,3H | 5G,3H | 4G | 4G | 3G | 4G,3H | 3G | 3G |
| Cassia | 5G | 6G | 7G | 7G | 6G | 8G,4C | 5G | 9G,8C | 7G | 9G,8C |
| Teaweed | 3G | 4G,3H | 5G,3H | 6G,4C | 5G | 8G,8C | 4G | 9G,9C | 3G | 4G |
| Velvetleaf | 6G,5H | 8G,5H | 7G,5H | 8G,8C | 5G,3H | 6G,5H | 5G,5H | 7G,5H | 3H | 5G,3H |
| Jimsonweed | 3G | 8G,3H | 7G | 8G,7C | 8G | 9G,8C | 5G,3C | 6G,5C | 2G | 8G,5C |
| Soybean | 2G | 4G,2H | 5G,3H | 7G,5H | 5G | 7G,5H | 4G,2H | 7G,7C | 4G,2H | 6G,5C |
| Rice | 7G | 10C | 10E | 10E | 10E | 10E | 8G | 10E | 8G,3H | 10E |
| Wheat | 2G | 7G,3H | 8G | 9G,8C | 6G | 8G,8C | 2G | 3G | 2G | 3G |

Test C

Twenty-five cm diameter plastic pots filled with Fallsington silt loam were planted with soybeans, cotton, alfalfa, corn, rice, wheat, sorghum, velvetleaf (*Abutilon theophrasti*), sesbania (*Sesbania exaltata*), sicklepod (*Cassia obtusifolia*), morningglory (*Ipomoea hederacea*), jimsonweed (*Datura stramonium*), cocklebur (*Xanthium pensylvanicum*), crabgrass (Digitaria sp.), nutsedge (*Cyperus rotundus*), barnyardgrass (*Echinochloa crusgalli*), johnsongrass (*Sorghum halepense*), field bindweed (*Convolvulus arvensis*), giant foxtail (*Setaria faberii*) and wild oats (*Avena fatua*). Approximately 2½ weeks after planting, the young plants and the soil around them were sprayed overall with the test chemicals dissolved in a non-phytotoxic solvent. Fourteen days after treatment, all species were compared to untreated controls and visually rated for response to treatment. The rating system was as described previously for Test A. The data are presented in Table C. Again, several of the compounds are characterized by a very high level of post-emergence activity.

Test D

Two ten-inch in diameter plastic pans lined with polyethylene liners were filled with prepared Woodstown sandy loam. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descurainia pinnata*), cleavers *Galium aparine*, tumble mustard (*Sisymbrium altissium*), kochia (*Kochia scoparia*), shepherd's purse (*Capsella bursapastoris*), *Matricaria inodora*, black nightshade (*Solanum nigrum*), yellow rocket (*Barbarea vulgaris*), rapeseed (*Brassica napus*) and wild buckwheat (*Polygonum convolvulus*). The above two pans were treated pre-emergence. At the same time two pans in which the above plant species were growing were tested post-emergence. Plant height at the time of treatment ranged from 1-15 cm depending on plant species.

The compounds applied were diluted with a non-phytotoxic solvent and sprayed over-the-top of the pans. An untreated control and a solvent alone control were included for comparison. All treatments were maintained in the greenhouse for 19-21 days at which time the treatments were compared to the controls and the effects visually rated. The recorded data are presented in Table D.

TABLE D

| | Compound 1 | | | |
|---|---|---|---|---|
| | Pre-Emergence | | Post-Emergence | |
| Rate kg/ha | 0.015 | 0.06 | 0.015 | 0.06 |
| wheat | 1G | 5G | 0 | 7G |
| barley | 1G | 5G | 0 | 6G |
| wild oats | 1G | 7G | 1C | 8G |
| downy brome | 5G | 7G | 8G | 7G |
| cheatgrass | 6G | 9G | 3C,8G | 8C,9G |
| blackgrass | 5G | 8G | 2C,7G | 3C,8G |
| annual bluegrass | 3G | 7G | 2C,7G | 8C,9G |
| green foxtail | 0 | 2G | 2C,2G | 2C,8G |
| quackgrass | 2G | 8G | 7G | 9C,9G |
| Italian ryegrass | 3G | 2C,8G | 2C,8G | 8C,8G |
| ripgut brome | 6G | 2C,8G | 1C,7G | 8C,9G |
| Russian thistle | 0 | 2G | 0 | 2C,2G |
| tansy mustard | 9G | 9C | 5C,7G | 9C,9G |
| *Galium aparine* | 2C | 2U,5G | 3G | 7G |
| tumble mustard | 3C,8G | 9C | 8G | 10C |
| kochia | 7G | 8G | 6G | 5C,8G |
| shepherd's purse | 8G | 9C | 6G | 8G |
| *Matricaria inodora* | 7G | 9G | 0 | 0 |
| black nightshade | 8G | 8G | 6G | 7G |
| yellow rocket | 7G | 8G | 4G | 2U,7G |
| rapeseed | 7G | 9G | 7G | 10C |
| wild buckwheat | 3G | 4G | 1C,3G | 2C,7G |

TABLE C

| | Over-the-Top Soil/Foliage Treatment | | | | | | | | | | |
|---|---|---|---|---|---|---|---|---|---|---|---|
| | Compound 1 | | | Compound 2 | | Compound 3 | | Compound 5 | | | Compound 6 | |
| Rate kg/ha | .063 | .016 | .004 | .063 | .016 | .063 | .016 | .063 | .016 | .004 | .063 | .016 |
| Soybeans | 8G,2C | 7G | 0 | 10G,4C | 9G,4C | 10G,5C | 9G,2C | 9G,4C | 8G,2C | 6G | 9G,2C | 9G,2C |
| Velvetleaf | 9G | 7G | 3G | 9G | 9G,4C | 9G,3C | 6G | 10C | 4G | 5G | 7G | 0 |
| Sesbania | 9G,2C | 8G | 4G | 10C | 10C | 10C | 9G,3C | 10C | 9G,4C | 7G | 10C | 8G |
| Cassia | 8G | 7G | 0 | 9G | 3G | 9G,3C | 2G | 9G | 3G | 4G | 7G | 0 |
| Cotton | 9G,2C | 9G | 0 | 10C | 8G,8C | 10C | 2G | 10C | 5G | 2G | 9G,2C | 7G |
| Morningglory | 4G | 6G | 0 | 8G | 8G | 9G | 0 | 8G | 3G | 0 | 6G | 2G |
| Alfalfa | 5G | 5G | 0 | 9G,9C | 8G,4C | 9G,9C | 3G | 9G,9C | 5G | 0 | 8G,6C | 0 |
| Jimsonweed | 4G | 5G | 0 | 9G | 7G | 10C | 7G | 9G,1C | 9G | 2G | 9G | 4G |
| Cocklebur | 8G | 8G | 0 | 9G | 0 | 9G | 4G | 6G | — | 0 | 5G | 1G |
| Sunflower | 10P | 8G,3C | 2G | 9G,9C | 7G,5C | 8G | 4G | 8G,1H | 6G,1H | 1H | 4G,1H | 0 |
| Mustard | 8G | 8G,3C | 0 | 9G,9C | 10C | 9G,9C | 9G | 10C | 9G,3C | 5G | 10C | 5G |
| Sugarbeets | 7G | 7G | 0 | 9G | 9G | 10C | 8G | 10C | 8G | 8G | 10C | 8G,2C |
| Corn | 8G,4U | 6G,3H | 3G,3H | 9G,2C | 9G,2C | 8G,5C | 8G | 8G,3C | 7G,3H | 2G,2H | 8G,8C | 7G,2H |
| Crabgrass | 0 | 0 | 0 | 6G | 2G | 0 | 0 | 0 | 0 | 0 | 0 | 0 |
| Rice | 7G,3C | 4G,2C | 2G | 9G,8C | 9G,7C | 7G | 3G | 6G | 2G | 0 | 8G | 3G |
| Nutsedge | 9G,4C | 7G,2C | 5G,1H | 9G,9C | 8G | 7G | 3G | 3G | 9G | 5G | 3G | 0 |
| Barnyardgrass | 9G,4C | 7G,2C | 3G,2H | 9G,9C | 9G,8C | 9G,9C | 9G,9C | 7G | 0 | 0 | 9G,6C | 3G |
| Wheat | 7G | 5G | 3G | 7G,6U | 7G,6C | 9G,9C | 6G | 7G | 2G | 0 | 8G,2C | 4G |
| Giant foxtail | 7G | 4G | 2G | 9G,7C | 9G,2C | 9G,4C | 7G | 6G | 0 | 0 | 5G | 4G |
| Wild Oats | 7G,2C | 6G | 3G,2C | 8G | 8G | 7G | 5G | 0 | 3G | 0 | 4G | 0 |
| Sorghum | 8G,2U | 6G | 6G | 8G,4C | 9G | 8G,6C | 8G | 7G,2U | 5G,1H | 0 | 7G | 5G |
| Johnsongrass | 6G,5U | 7G,2U | 7G,2C | 8G,4U | 8G,4U | 8G,6U | 8G,3U | 6G | 4G | 0 | 7G,2U | 3G |
| Field Bindweed | 3G | 2G | 0 | 8G | 4G | 4G | 7G | 4G | 0 | 0 | 7G | 0 |

What is claimed is:

1. A compound of the formula:

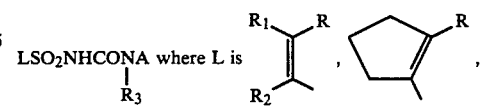

$LSO_2NHCONA$ where L is
$R_3$

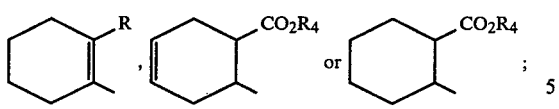

R is F, Cl, Br, $C_1-C_3$ alkyl, $CO_2R_4$, $C(O)SR_8$, $C(O)NR_5R_6$ or $S(O)_mR_7$;
$R_1$ is H, F, Cl, Br or $C_1-C_3$ alkyl;
$R_2$ is H, F, Cl, Br or $C_1-C_3$ alkyl;
$R_3$ is H or $CH_3$;
$R_4$ is $C_1-C_4$ alkyl, $CH_2CH_2OCH_3$, $CH_2CH_2Cl$ or $CH_2CH=CH_2$;
$R_5$ is H or $C_1-C_3$ alkyl;
$R_6$ is $C_1-C_3$ alkyl; or
$R_5$ and $R_6$ may be taken together to form $-(CH_2)_4-$, $-(CH_2)_5-$ or $-(CH_2)_2O(CH_2)_2-$;
$R_7$ is $C_1-C_3$ alkyl;
$R_8$ is $C_1-C_4$ alkyl;
m is 0, 1 or 2;
A is

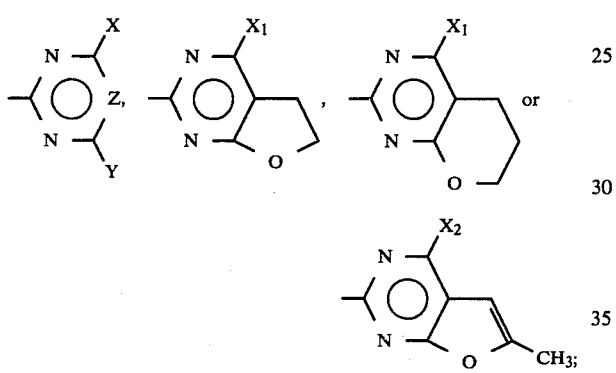

X is Cl, $CH_3$ or $OCH_3$;
Y is $CH_3$, $C_2H_5$, $CH_2OCH_3$, $OCH_3$, $OC_2H_5$, $NH_2$, $NHCH_3$, $N(CH_3)_2$, $CH(OCH_3)_2$ or

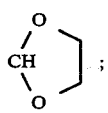

Z is CH;
$X_1$ is H, Cl, $CH_3$, $OCH_3$ or $OC_2H_5$; and
$X_2$ is $CH_3$, $C_2H_5$, $OCH_3$ or $OC_2H_5$;
and their agriculturally suitable salts; provided that:
(1) when R is halogen and $R_1$ and/or $R_2$ are halogen, then the values of R, $R_1$ and $R_2$ must be the same;
(2) when $R_1$ and $R_2$ are halogen, then the values of $R_1$ and $R_2$ must be the same;
(3) the total number of carbon atoms of $R_5$ and $R_6$ is less than or equal to 5;
(4) when X is Cl, then Z is CH and Y is $OCH_3$, $NH_2$, $NHCH_3$ or $N(CH_3)_2$;
(5) $R_1$ and $R_2$ are not simultaneously H; and
(6) when L is

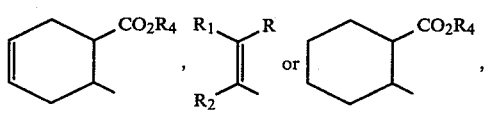

then A is

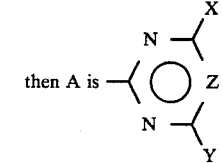

2. Compounds of claim 1 where L is

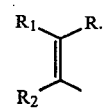

3. Compounds of claim 2 where:
R is Cl, Br, $C_1-C_3$ alkyl, $CO_2R_4$ or $SO_2R_7$;
$R_4$ is $C_1-C_3$ alkyl; and
$R_3$ is H.
4. Compounds of claim 3 where R is $CO_2R_4$.
5. Compounds of claim 1 where L is

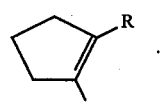

6. Compounds of claim 5 where
R is $CO_2R_4$;
$R_4$ is $C_1-C_3$ alkyl; and
$R_3$ is H.
7. Compounds of claim 6 where A is

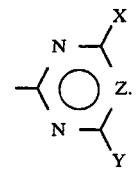

8. Compounds of claim 1 where L is

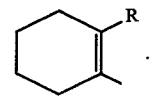

9. Compounds of claim 8 where
R is $CO_2R_4$;
$R_4$ is $C_1-C_3$ alkyl; and
$R_3$ is H.
10. Compounds of claim 11 where A is

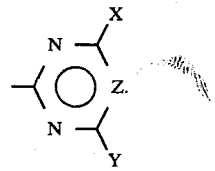

11. The compound of claim 1, 2-[[(4,6-dimethyl-pyrimidin-2-yl)aminocarbonyl]aminosulfonyl]-1-cyclopentene-1-carboxylic acid, methyl ester.

12. The compound of claim 1, 2-[[(4-methoxy-6-methylpyrimidin-2-yl)aminocarbonyl]aminosulfonyl]-1-cyclopentene-1-carboxylic acid, methyl ester.

13. The compound of claim 1, 2-[[(4,6-dimethoxypyrimidin-2-yl)aminocarbonyl]aminosulfonyl]-1-cyclopentene-1-carboxylic acid, methyl ester.

14. A composition suitable for controlling the growth of undesired vegetation which comprises an effective amount of a compound of claim 1 and at least one of the following: surfactant, solid or liquid inert diluent.

15. A composition suitable for controlling the growth of undesired vegetation which comprises an effective amount of a compound of claim 2 and at least one of the following: surfactant, solid or liquid inert diluent.

16. A composition suitable for controlling the growth of undesired vegetation which comprises an effective amount of a compound of claim 3 and at least one of the following: surfactant, solid or liquid inert diluent.

17. A composition suitable for controlling the growth of undesired vegetation which comprises an effective amount of a compound of claim 4 and at least one of the following: surfactant, solid or liquid inert diluent.

18. A composition suitable for controlling the growth of undesired vegetation which comprises an effective amount of a compound of claim 5 and at least one of the following: surfactant, solid or liquid inert diluent.

19. A composition suitable for controlling the growth of undesired vegetation which comprises an effective amount of a compound of claim 6 and at least one of the following: surfactant, solid or liquid inert diluent.

20. A composition suitable for controlling the growth of undesired vegetation which comprises an effective amount of a compound of claim 7 and at least one of the following: surfactant, solid or liquid inert diluent.

21. A composition suitable for controlling the growth of undesired vegetation which comprises an effective amount of a compound of claim 8 and at least one of the following: surfactant, solid or liquid inert diluent.

22. A composition suitable for controlling the growth of undesired vegetation which comprises an effective amount of a compound of claim 9 and at least one of the following: surfactant, solid or liquid inert diluent.

23. A composition suitable for controlling the growth of undesired vegetation which comprises an effective amount of a compound of claim 10 and at least one of the following: surfactant, solid or liquid inert diluent.

24. A composition suitable for controlling the growth of undesired vegetation which comprises an effective amount of the compound of claim 11 and at least one of the following: surfactant, solid or liquid inert diluent.

25. A composition suitable for controlling the growth of undesired vegetation which comprises an effective amount of the compound of claim 12 and at least one of the following: surfactant, solid or liquid inert diluent.

26. A composition suitable for controlling the growth of undesired vegetation which comprises an effective amount of the compound of claim 13 and at least one of the following: surfactant, solid or liquid inert diluent.

27. A method for controlling the growth of undesired vegetation which comprises applying to the locus to be protected an effective amount of a compound of claim 1.

28. A method for controlling the growth of undesired vegetation which comprises applying to the locus to be protected an effective amount of a compound of claim 2.

29. A method for controlling the growth of undesired vegetation which comprises applying to the locus to be protected an effective amount of a compound of claim 3.

30. A method for controlling the growth of undesired vegetation which comprises applying to the locus to be protected an effective amount of a compound of claim 4.

31. A method for controlling the growth of undesired vegetation which comprises applying to the locus to be protected an effective amount of a compound of claim 5.

32. A method for controlling the growth of undesired vegetation which comprises applying to the locus to be protected an effective amount of a compound of claim 6.

33. A method for controlling the growth of undesired vegetation which comprises applying to the locus to be protected an effective amount of a compound of claim 7.

34. A method for controlling the growth of undesired vegetation which comprises applying to the locus to be protected an effective amount of a compound of claim 8.

35. A method for controlling the growth of undesired vegetation which comprises applying to the locus to be protected an effective amount of a compound of claim 9.

36. A method for controlling the growth of undesired vegetation which comprises applying to the locus to be protected an effective amount of a compound of claim 10.

37. A method for controlling the growth of undesired vegetation which comprises applying to the locus to be protected an effective amount of the compound of claim 11.

38. A method for controlling the growth of undesired vegetation which comprises applying to the locus to be protected an effective amount of the compound of claim 12.

39. A method for controlling the growth of undesired vegetation which comprises applying to the locus to be protected an effective amount of the compound of claim 13.

* * * * *